(12) United States Patent
Sahadevan

(10) Patent No.: US 8,139,714 B1
(45) Date of Patent: Mar. 20, 2012

(54) FEW SECONDS BEAM ON TIME, BREATHING SYNCHRONIZED IMAGE GUIDED ALL FIELDS SIMULTANEOUS RADIATION THERAPY COMBINED WITH HYPERTHERMIA

(76) Inventor: Velayudhan Sahadevan, Beckley, WV (US)

( * ) Notice: Subject to any disclaimer, the term of this patent is extended or adjusted under 35 U.S.C. 154(b) by 0 days.

(21) Appl. No.: 12/459,120

(22) Filed: Jun. 25, 2009

(51) Int. Cl.
*A61N 5/10* (2006.01)
*G01N 23/04* (2006.01)

(52) U.S. Cl. .................. 378/65; 378/63; 378/95
(58) Field of Classification Search ............ 378/63, 378/65, 95
See application file for complete search history.

(56) References Cited

U.S. PATENT DOCUMENTS

| | | | |
|---|---|---|---|
| 2,139,966 A | 3/1935 | Lobell | |
| 2,624,013 A | 5/1949 | Marks | |
| 4,726,046 A | 2/1988 | Nunan | |
| 4,780,898 A | 10/1988 | Sundqvist | |
| 4,998,268 A * | 3/1991 | Winter | 378/63 |
| 5,339,347 A | 8/1994 | Slatkin et al. | |
| 5,537,452 A | 7/1996 | Shepperd et al. | |
| 5,553,618 A * | 9/1996 | Suzuki et al. | 600/411 |
| 5,590,653 A * | 1/1997 | Aida et al. | 600/411 |
| 5,627,870 A | 5/1997 | Kopecky | |
| 5,802,136 A * | 9/1998 | Carol | 378/65 |
| 6,104,779 A * | 8/2000 | Shepherd et al. | 378/65 |
| 6,259,762 B1 * | 7/2001 | Pastyr et al. | 378/65 |
| 6,366,798 B2 * | 4/2002 | Green | 600/411 |
| 6,512,813 B1 * | 1/2003 | Krispel et al. | 378/65 |
| 6,968,036 B2 * | 11/2005 | Carlsson et al. | 378/65 |
| 7,564,945 B2 * | 7/2009 | Kim | 378/65 |
| 7,656,999 B2 * | 2/2010 | Hui et al. | 378/65 |
| 7,741,624 B1 * | 6/2010 | Sahadevan | 250/494.1 |
| 2006/0079763 A1 * | 4/2006 | Jeung et al. | 600/428 |
| 2007/0173680 A1 * | 7/2007 | Rioux et al. | 600/2 |

OTHER PUBLICATIONS

U.S. Appl. No. 60/790,192, filed Apr. 6, 2006, Sahadevan Velayudhan.
U.S. Appl. No. 11/784,398, filed Apr. 5, 2007, Sahadevan Velayudhan.
U.S. Appl. No. 11/974,876, filed Oct. 15, 2007, Sahadevan Velayudhan.
U.S. Appl. No. 60/872,117, filed Nov. 30, 2006, Sahadevan Velayudhan.
U.S. Appl. No. 60/998,063, filed Nov. 27, 2007, Sahadevan Velayudhan.
U.S. Appl. No. 60/927,622, filed May 3, 2007, Sahadevan Velayudhan.
U.S. Appl. No. 12/151,014, filed May 3, 2008, Sahadevan Velayudhan.
Hall EJ, Hyperthermia, in The Radiobiology for the Radiologist, Fifth Edition, 2000, p. 510 Lippencott & Wilkins, Philadelphia, USA.

(Continued)

*Primary Examiner* — Edward Glick
*Assistant Examiner* — Thomas R Artman

(57) ABSTRACT

This invention relates to single session image guided all field simultaneous radiation therapy combined with hyperthermia. Hyperthermia renders the radiation resistant cells as more radiation sensitive cells. The high and super-high dose rate radiation greatly improves the RBE of the photon radiation. It also minimizes photon radiation therapy's OER and cell cycle dependent tumor cell kill by minimizing the repair capacity of cell after photon radiation. Single session hyperthermia and radiation therapy overcomes the thermotolerance-associated inefficiency of hyperthermia treatment as it is when hyperthermia is combined with fractionated, lower dose rate radiation. The synergetic effects of sublethal damage repair inhibiting single session hyperthermia-combined with high dose and dose rate single session radiation therapy, and combined chemotherapy brings the photon radiation therapy's tumor cure and control capabilities closer to high LET radiation therapy.

18 Claims, 20 Drawing Sheets

OTHER PUBLICATIONS

Hall EJ, Repair of radiation damage and Dose Rate Effect, in The Radiobiology for the Radiologist, Fifth Edition, 2000, p. 81 Lippencott & Wilkins.

Regis J et al, Prospective controlled Traial of Gamma Knife Surgery for Trigeminal Neuralgia, J. Nerosurg 104: 913-924, 2006.

Shrive DC et al Fig. 25-4, B, p. 552; Textbook of Radiation Oncology: Radiosurgery, p. 549-564, ed. Steven A. Liebel and Theodore L., 2004, p. 549-564, Saunders, Philadelphia.

Balamucki, CJ et al, Does dose rate affect efficacy? The outcome of 256 Gamma Knife surgery Procedures for—J Neurosurg 105: 730-735, 2006.

Hall EJ, Linear Energy Transfer and—, in The Radiobiology for the Radiologist, Fifth Edition, 2000, p. 114 Lippencott & Wilkins, Philadelphia, USA.

Narkita M., Coley's Toxins/Issel's Fever Therapy Cancer Guide Alternative and Complementray Therapies, in Internet, Apr. 1996.

BSD Medical, report—Targeted Hyperthermia Therapy Highlites, European Radiation Oncology Convention, Salt Lake City, Internet, Nov. 2006.

Sneed PK. et al, Hyperthermia, Textbook of Radiation Oncology: Radiosurgery, p. 1569-1596, ed. Steven A. Liebel and Theodore L., 2004, p. 549-564, Saunders, Philadelphia.

Intraoperative mobile magnetic resonance imaging for craniotomy—Canadian Journal of Anesthesia 49, 4: p. 420-426, 2002.

Khan, FM, Measurement of absorbed dose, in The Physics of Radiation TherapyLippencott Williams & Wilkins, p. 141, 2003.

Khan FM, in The Physics of Radiation Therapy, Chapter 10, A System of Dosimetric Calculations, A. Accelerator Calculations,—Lippencott Williams & Wilkin, p. 217, 2003.

Xia P et al, Three dimensional conformal Radiotherapy and Intensity Modulated—; Textbook of Radiation Oncology: Radiosurgery, p. 177, ed. Steven A. Liebel and Theodore L.

* cited by examiner

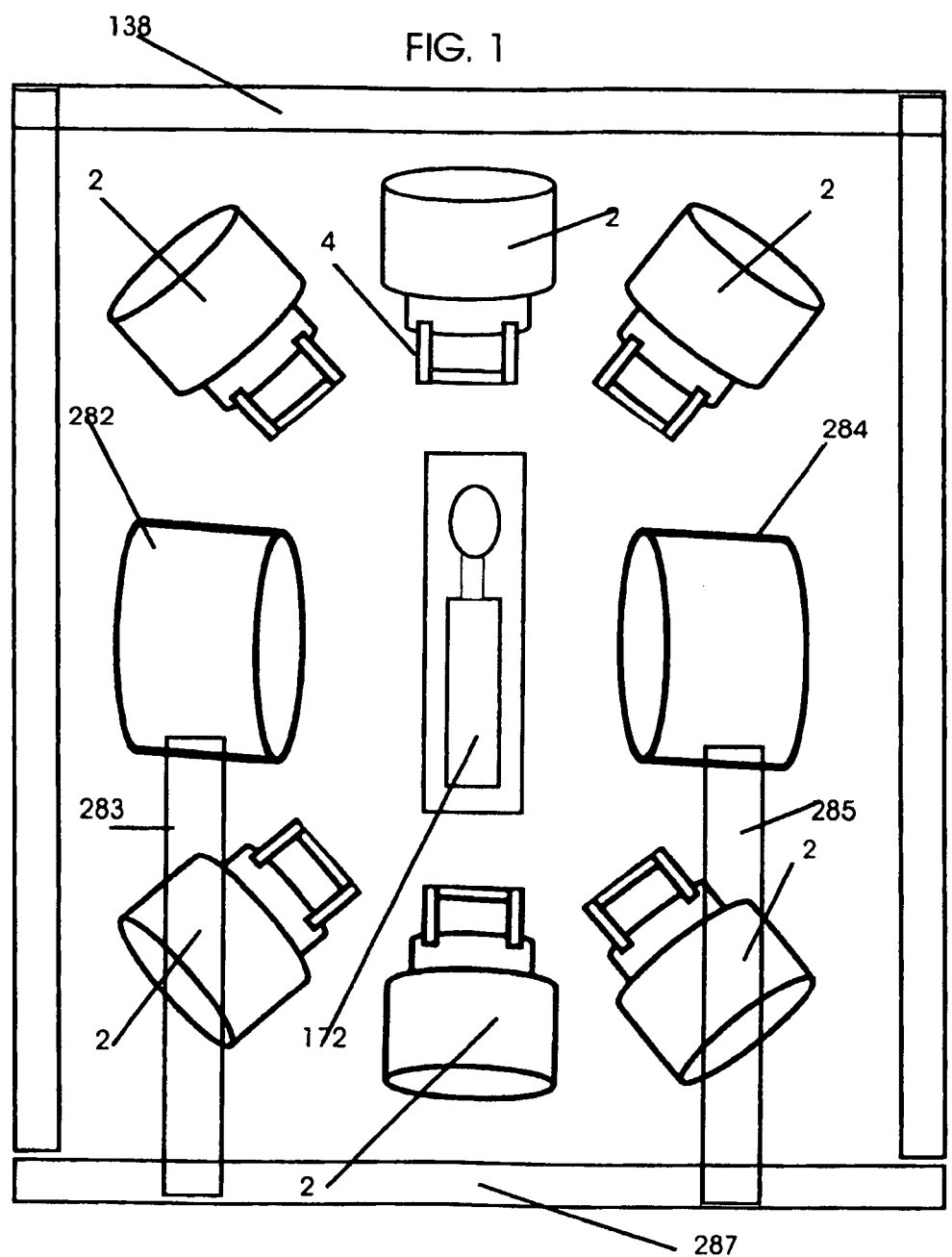

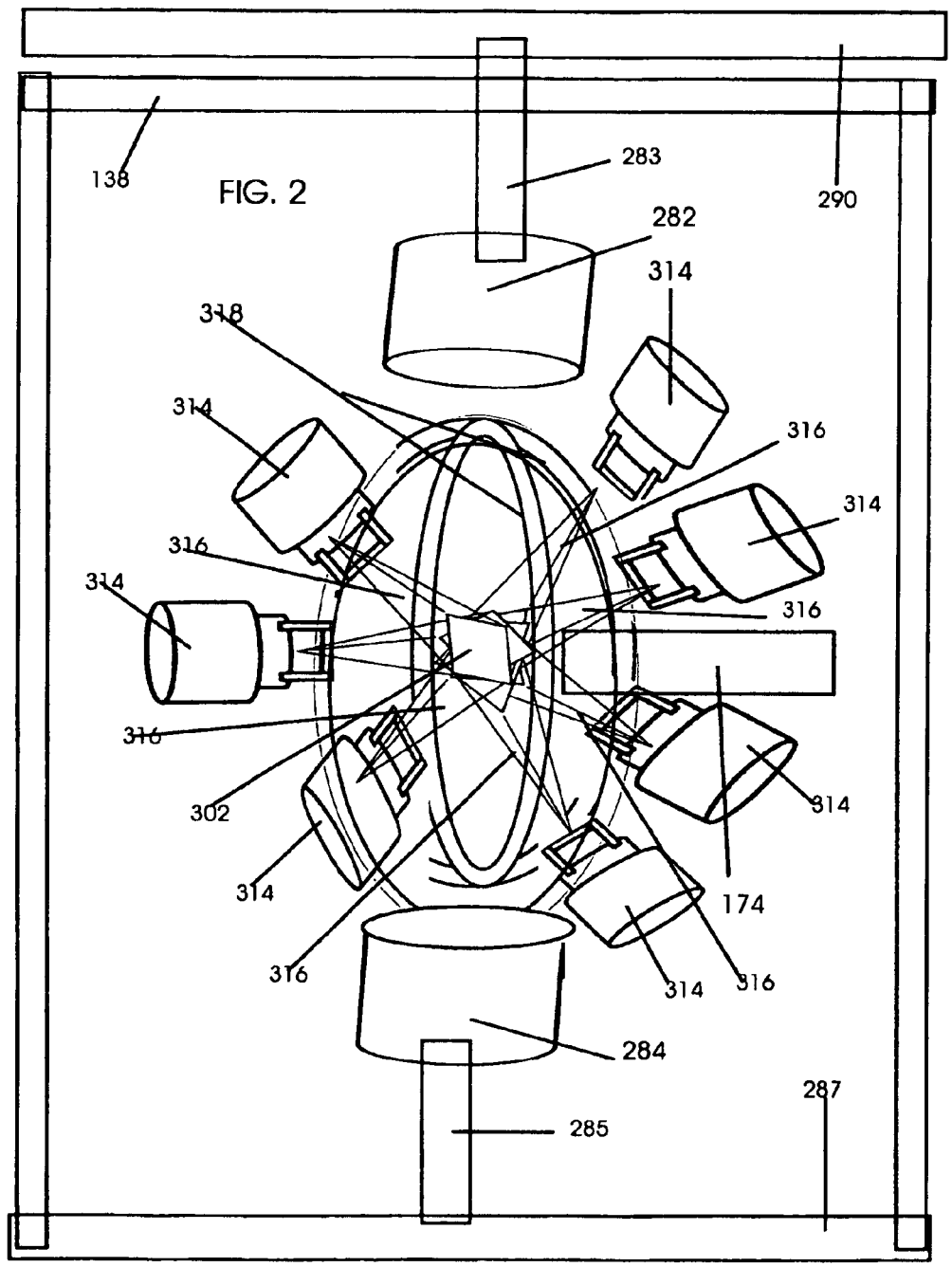

FIG. 3E
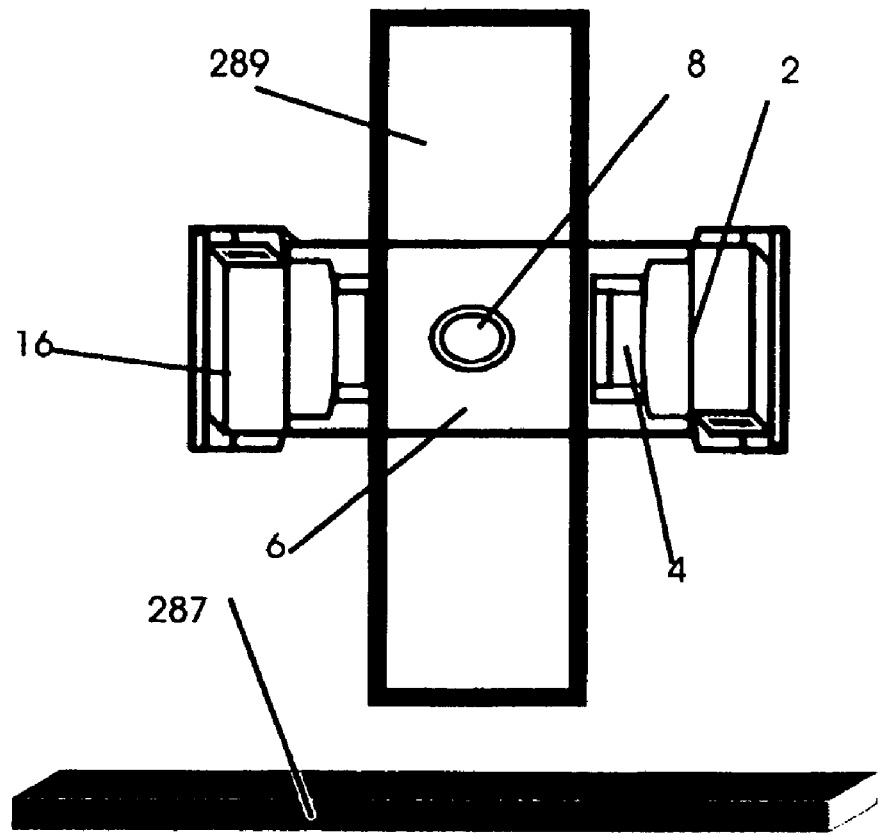
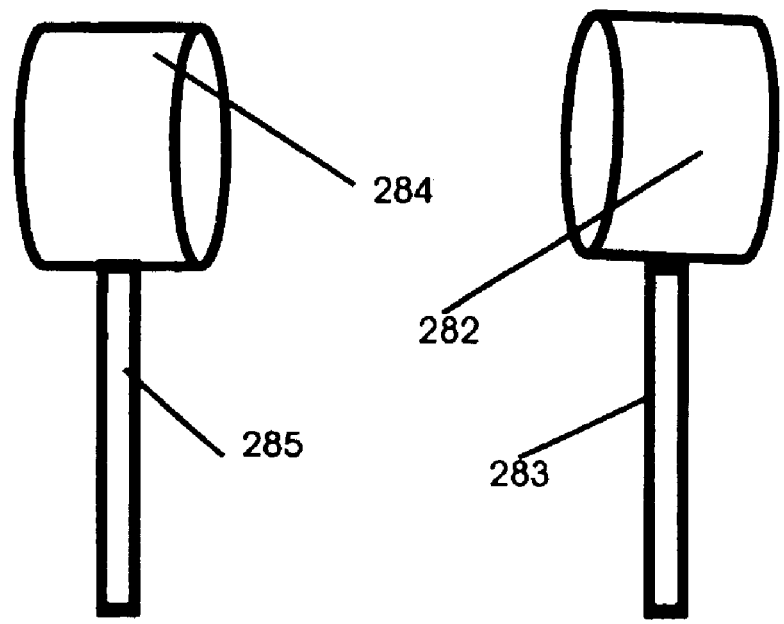

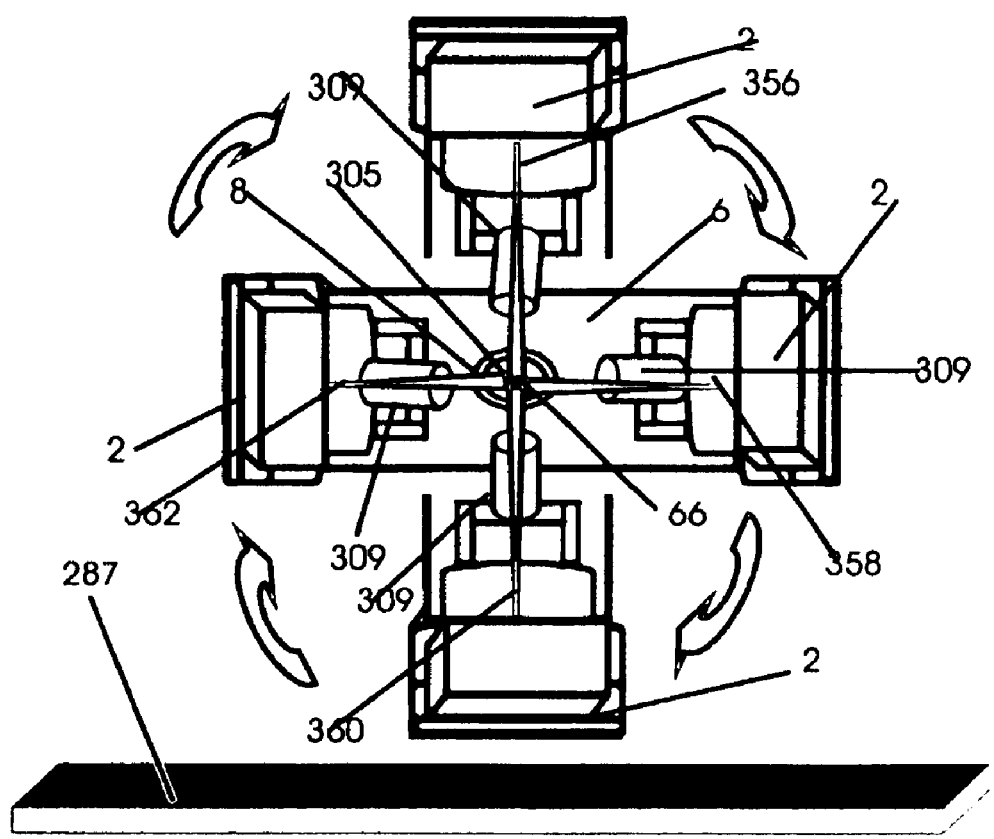
FIG. 3F
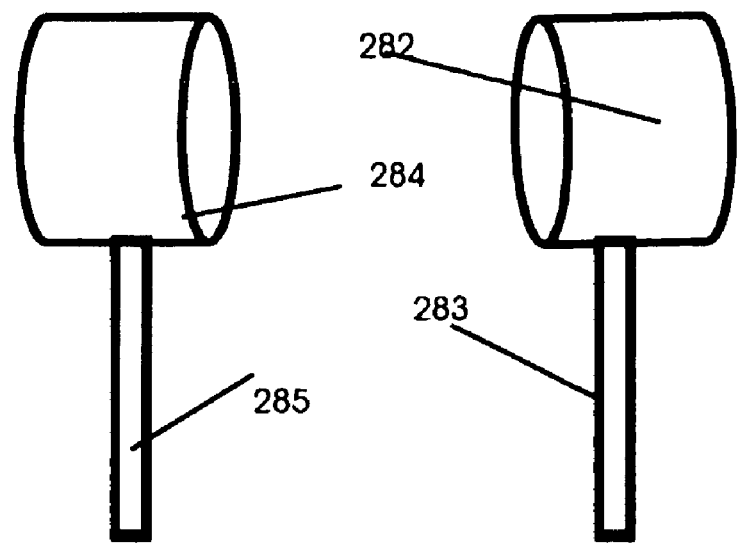

FIG. 3-I
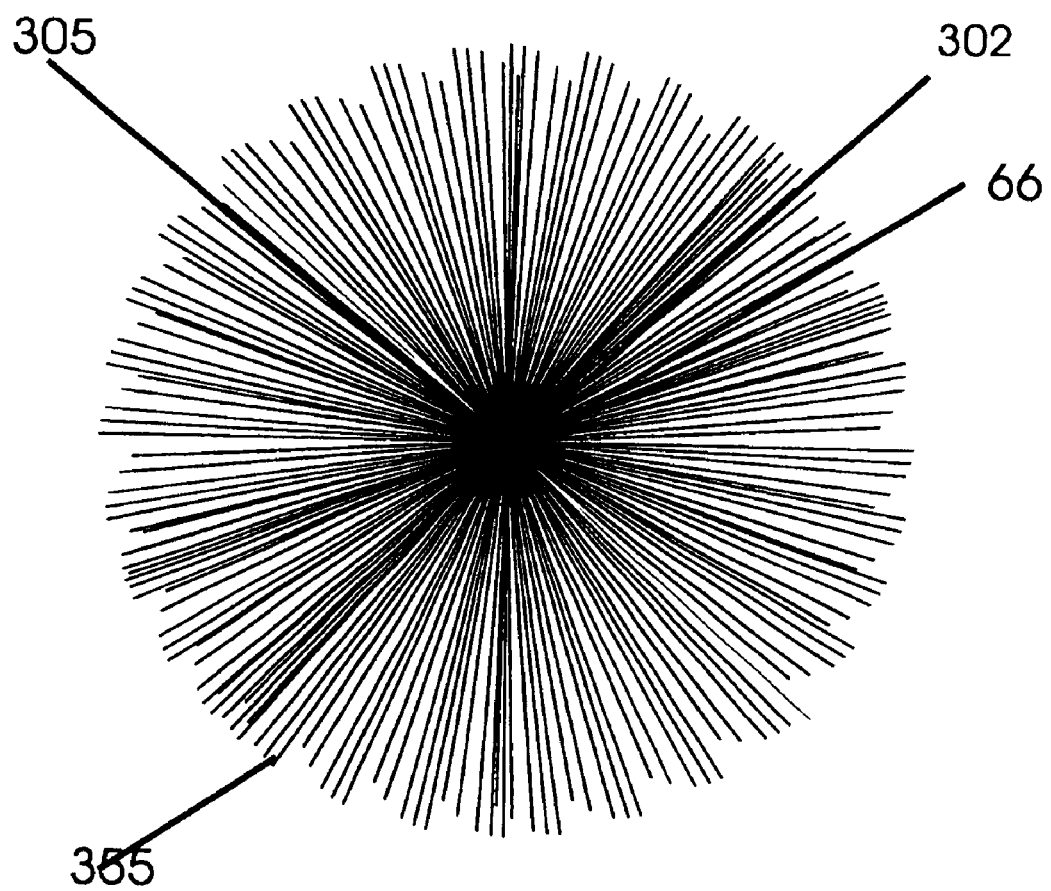

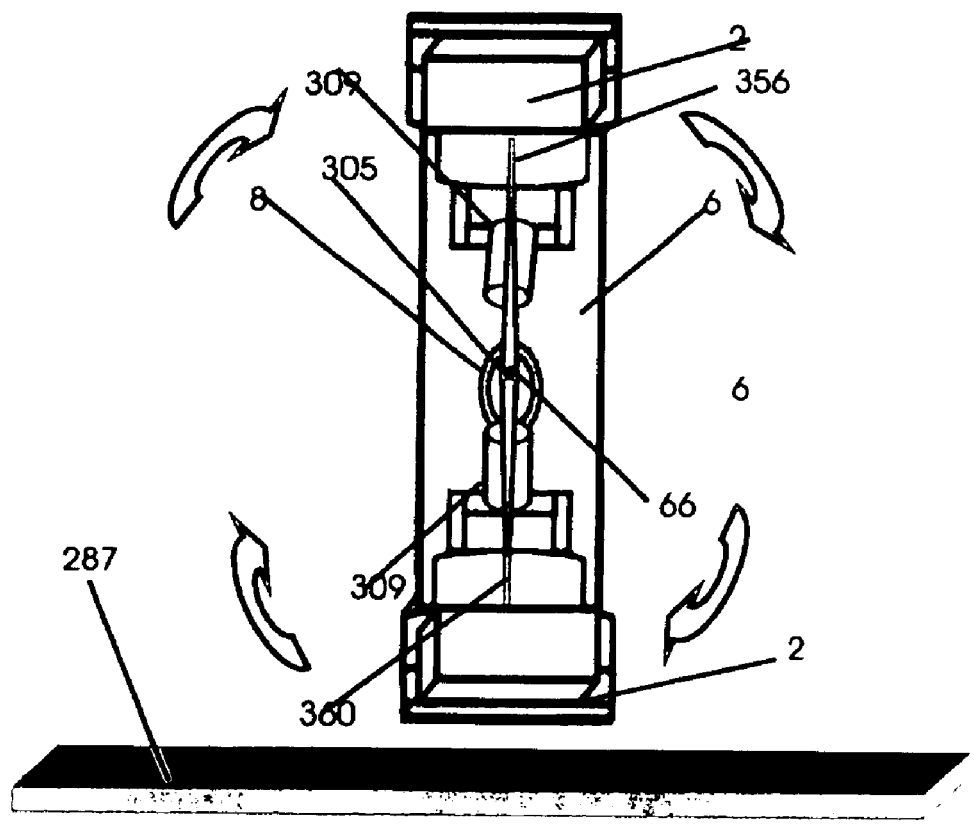
FIG. 3K
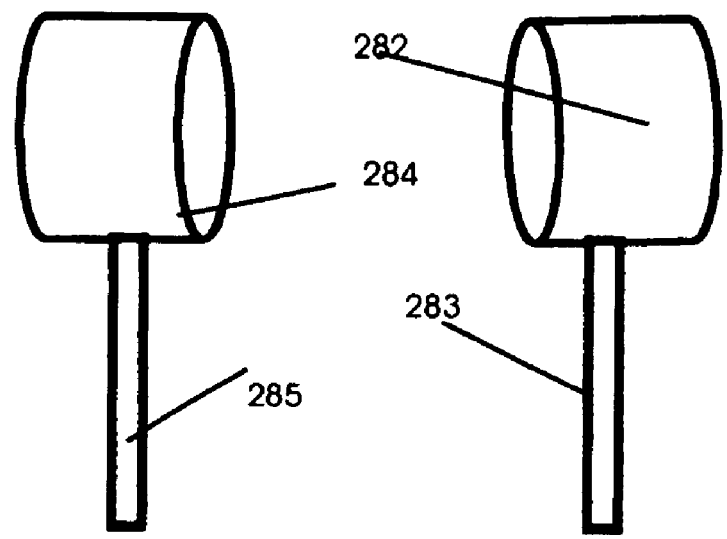

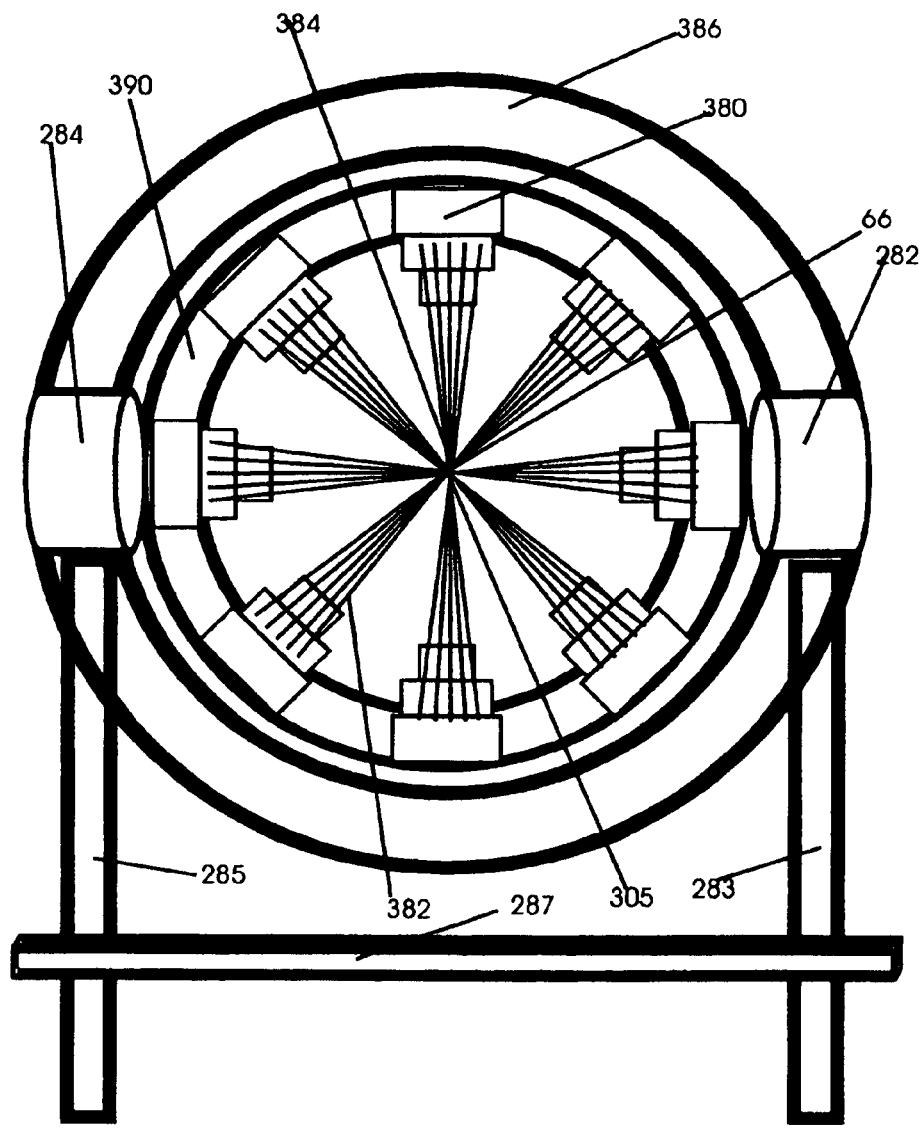

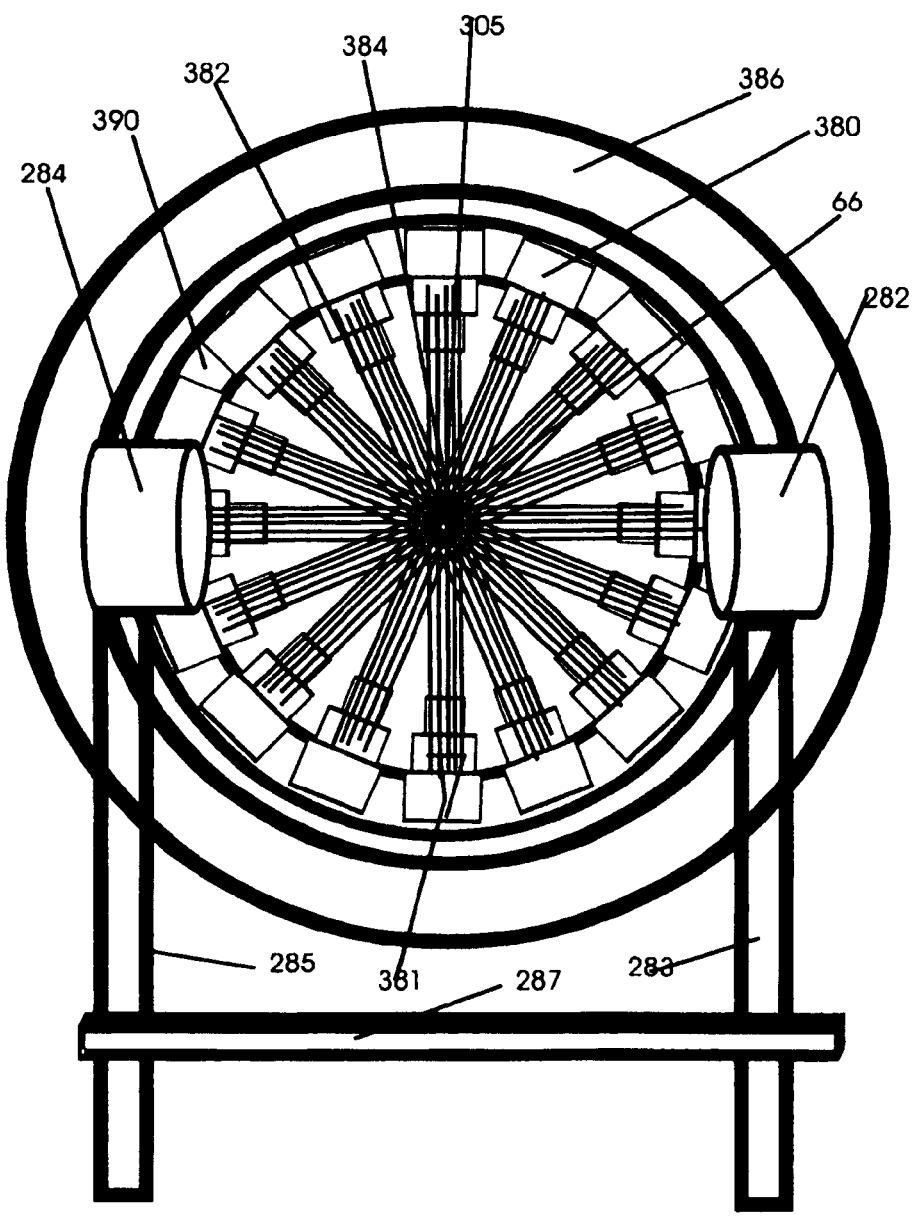
FIG. 3N2

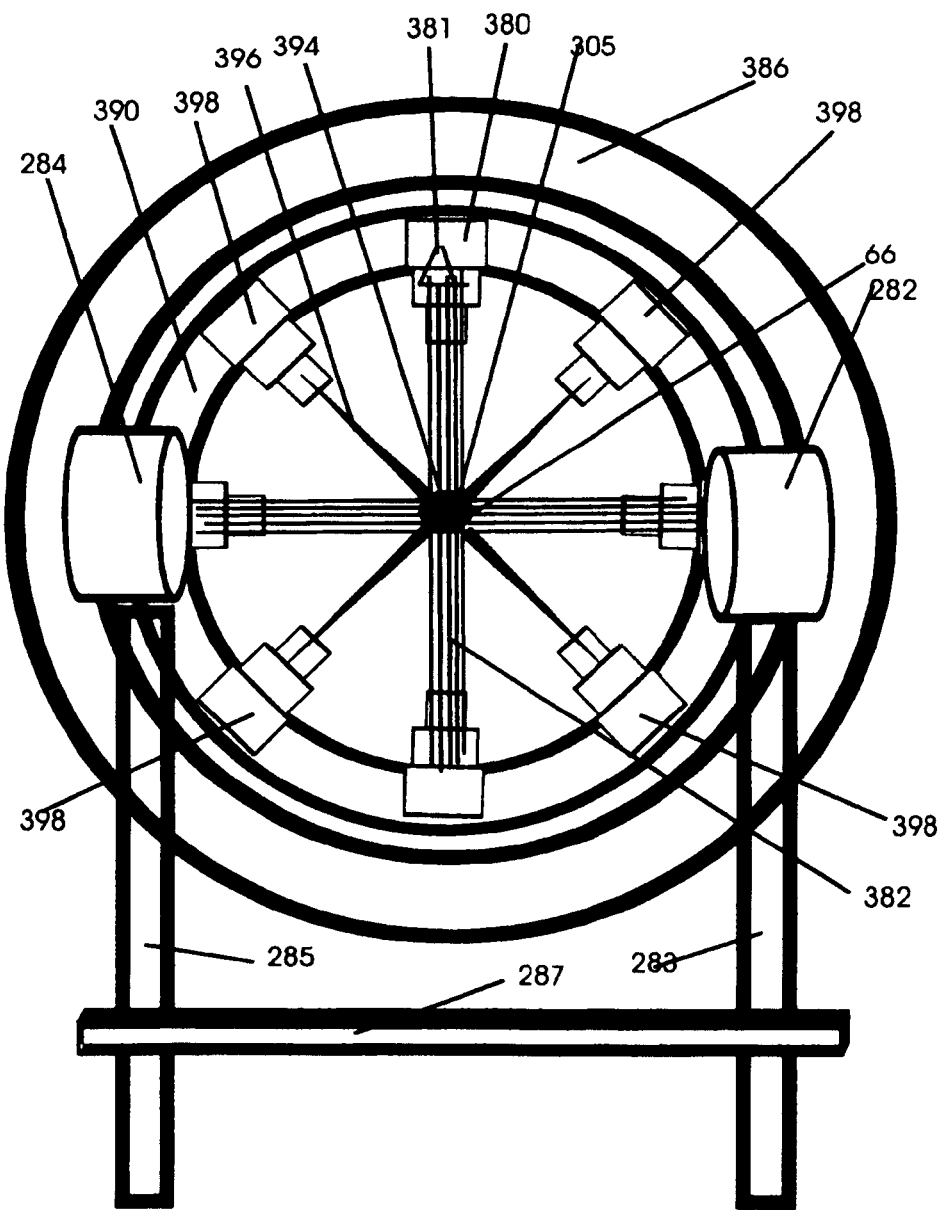
FIG. 3N3

FEW SECONDS BEAM ON TIME, BREATHING SYNCHRONIZED IMAGE GUIDED ALL FIELDS SIMULTANEOUS RADIATION THERAPY COMBINED WITH HYPERTHERMIA

CROSS REFERENCE TO RELATED APPLICATIONS

This Application claims the benefit of US provisional patent application, 60/790,192, filed on Apr. 6, 2006 "Multiple medical accelerators and kV-CT incorporated radiation therapy device and semi-automated custom reshapeable blocks for all field synchronous image guided 3-D conformal-intensity modulated radiation therapy" (7) and its regular patent application Ser. No. 11/784,398 filed on Apr. 5, 2007 (8), its continuation application Ser. No. 11/974,876 filed on Oct. 15, 2007 (9), Provisional Patent Application 60/872,117, filed on Nov. 30, 2006 "Lethal and Sublethal Damage Repair Inhibiting Image Guided Simultaneous All Field Divergent and Pencil Beam Photon and Electron Radiation Therapy and Radiosurgery" (10) and its non-provisional application Ser. No. 11/998,063 filed on Nov. 27, 2007 (11), Provisional Patent Application 60/927,622, filed on May 3, 2007 "Single session interactive image guided simulation, field shaping, treatment planning and ultra short duration, super-high biological dose rate all field simultaneous or sequential radiation therapy and radiosurgery" and its non-provisional application 12/151,014 filed on May 3, 2008 (13) which are incorporated herein.

FIELD OF INVENTION

This invention relates to few second duration beams on time simultaneous radiation therapy to all treatment fields combined with hyperthermia.

BACKGROUND OF THE INVENTION

Prior Art

Brachytherapy by treating a tumor by implanting multiple radioactive sources around the tumor bearing tissue has some similarity to simultaneous multiple field setup external beam radiation therapy to a tumor. Combined, each of such implanted radioactive source's simultaneous beams represents multiple simultaneous external beams. Multiple simultaneous external beams from multiple medical accelerators arranged at different angles and their beams converging on to the tumor could mimic simultaneous radiation from multiple radioactive sources implanted in a tumor. However this similarity between simultaneous beams from the implanted radioactive source and from multiple simultaneous external beams is very vague one. The conventional brachytherapy lasts 48-120 hours and high dose rate brachytherapy with 100 to 300 cGy/h and about 600 cGy/treatment lasts about 6 to 2 hours. In brachytherapy, the normal tissue adjacent to the tumor receives the same dose of simultaneous radiation as the tumor. Hence the normal tissue adjacent to the tumor is not spared from high dose radiation as in the case of radiation with multiple external simultaneous beams. The simultaneous beam brachytherapy is not like applying multiple field setup simultaneous external beam radiation therapy to a tumor that lasts for a few seconds.

Maurice A. Loebell in his U.S. Pat. No. 2,139,966 issued on Dec. 13, 1938 (1) described the use of multiple simultaneous beams to treat a tumor located below the skin and thereby to minimize the dose from such low energy x-rays to the skin. He described multiple tubes each with anode and cathode installed at small distance from each other in a treatmenthead like structure. Their simultaneous beams were focused at a point below the skin. It has no relevance to modern megavoltage radiation therapy. Also if it were a multiple filed setup radiation therapy, each field was to be treated separately and not simultaneously. Simultaneous radiation to all the treatment fields renders additive high dose rate at the focal point of all the simultaneous beams. Such high additive biological dose rate at the focal point improves the photon beam's radiobiological characteristics. Seventy years ago when the concept of megavoltage and high energy Linac x-ray beams were not even born, Loebell's patent taught a very innovative approach to treat a tumor by simultaneous multiple beams to minimize the toxic effects of radiation to normal tissue by radiating a tumor with then available superficial radiation therapy machines. However, for present radiation therapy practice, the Loebell's patent is irrelevant. It does not teach the use of multiple simultaneous megavoltage beams to treat all the treatment fields simultaneously to improve the radiobiological characteristics of megavoltage photon beams. The additive dose rate at the focal point by radiation of all the treatment fields simultaneously renders high and super-high dose rate at their combined focal point, which is adjusted to be the treatment site with the tumor. It enhances the tumor cell kill and tumor control than when each treatment field is treated sequentially.

Hirsch Marks, in his 1952 U.S. Pat. No. 2,624,013 (2) described the use of lead sheets with small cutouts to minimize dose to the skin while irradiating a large area of about 25 inches. The lead shield is covered with plastics or rubber and is placed above the skin. It filters the low energy superficial x-ray beams and reduces sixty percent of the dose to skin while treating "simultaneously" to a larger field. Such "simultaneous" beam treatment has no relevance to modern megavoltage radiation therapy. Marks patent does not teach the use of multiple simultaneous megavoltage beams to treat all the treatment fields simultaneously to improve the radiobiological characteristics of megavoltage photon beams.

Joseph S. Shepherd's and Rand Robert W's patent, U.S. Pat. No. 5,537,452 issued on Jul. 16, 1996 (3) teaches the use of megavoltage producing multiple $^{60}$Co sources arranged as separate sources at small distance from each other in a single treatmenthead. The focal point of each $^{60}$Co source within a treatment head is adjusted at the tumor site, which is below the skin. It minimizes the dose to the skin. Like the Loebell's patent Shepherd et al's patent does not teach the use of multiple simultaneous megavoltage beams to treat all the treatment fields simultaneously to improve the radiobiological characteristics of megavoltage photon beams. The additive dose rate at the focal point by radiation of all the treatment fields simultaneously renders high and super-high dose rate at their combined focal point that is adjusted to be the treatment site with the tumor. It enhances the tumor cell kill and tumor control than when each treatment field is treated sequentially.

Hans Sundqvist's patent, U.S. Pat. No. 4,780,898 issued on Oct. 25, 1988 (4) and Bernard Kopecky's patent, U.S. Pat. No. 5,627,870 issued on May 6, 1997 (5) teach the use a large number of gamma ray producing sources arranged as separate sources at small distance from each other in a semi spherical source-collimator structure. They are used to treat a tumor or other lesions located in the brain. It has a large number of simultaneous very low dose rate gamma rays. As they converge together at the focal point, their additive dose is sufficient to treat a lesion in the head. Such a treatment machine is illustrated in Bernard Kopecky's patent U.S. Pat. No. 5,627, 870. It is not suitable for treating tumors and lesions located at other sites in the body. Such gamma knife like structures with numerous gamma sources like $^{60}Co$ has combined dose rate of about 140-cGy/min (16, 18). This low dose rate has inferior radiobiological qualities. Because of the organ movement during respiration, treating a tumor precisely with such a machine is impossible. Because of the respiratory movement of the organ to be treated, the organ moves during prolonged radiation exposure time by such machines. It makes impossible to deliver precise therapeutic dose of radiation to a tumor located in such moving target. These machines cannot rotate to treat a tumor from multiple angles and multiple fields. Treating a tumor with this machine by multiple field setups and rotating the patent to treat each field is likewise impossible.

The U.S. Pat. No. 5,339,347 issued to Daniel N. Slatkin, Dilmanian F. Averham and Spanne Per 0 on Aug. 16, 1994 (6) teaches the use of multiple simultaneous microbeams to treat a tumor with minimal toxicity to normal tissue and to facilitate regeneration of the normal endothelial cells of the blood vessels that are in the radiation filed. The effects on regeneration of the tumor vascular endothelial cells and hence the tumor re-growth is not clarified in this patent. This patent refers to a number of prior art patents that produce microbeams from common x-ray beam by dividing the x-ray beam into microbeams of 50 to 500 μm wide. This is done with the aid various kinds of collimators with apertures ranging from 3-4 mm to 25 μm or by small micro fields. In radiation treatment with microbeams, parallel or near parallel micro beam radiation is delivered to the tumor as through microscopically segmented radiation fields. Each microbeam is about 20 to 200 μm wide. The unirradiated tissue in between the path of the microbeam is between 50 to 500 μm wide. This can leave unirradiated or minimally irradiated tumor tissue within an irradiated region of the tumor. The preferred energy of the beam is in the range of 50 to 150 keV. Thousands of microbeams are needed to treat a large tumor. A large tumor is treated sequentially by an array of microbeams as by treating a portion of the tumor with an array of micro beams and then moving the patient to treat another portion of the tumor. In this instance, it is a sequential, small field by small field treatment of a tumor. The alternative is the use of many bundles of microbeams generated with multiple apertures collimator for the passage of the x-ray beam. It results in multiple simultaneous microbeams. Still, a large tumor needs to be treated from various angles as by multiple field setups. Thus after treating a tumor with microbeams from one angle, say from 0° and then directing the beam from 90° angle will cause interrupted field by field treatment even when an array of simultaneous microbeams are produced with special collimators for the treatment of the entire or most of the tumor from any one angle at a time. Hence it still remains as a sequential treatment. Therefore, it suffers the radiobiological advantages of treating a tumor from multiple angles simultaneously and thereby with high and super-high additive dose rate. It is almost impossible to stop the displacement of the target tissue completely during the treatment setup and the beam on time of the micro beams. It would cause unintended high dose to both normal tissue and to tumor tissue. In cross firing computer modeled experiments with 8 cross-fired bundles of 100 keV microbeams in Example 3 in this patent the target dose at 7.5 cm depth was 48 Gy, which is 4,800 cGy. The dose proximal and distal to the target was 2.9 Gy, which is the normal tissue dose proximal and distal to the target. This patent does not describe if the cross firing beams from various angles were parallel opposed; most likely it is. Then the total dose to normal tissue at $D_{max}$ is the entrance $D_{max}$ dose plus the exit dose at $D_{max}$ from the parallel-opposed beams. Assuming the 290-cGy normal tissue dose is the single beam's $D_{max}$ dose, plus the exit dose at $D_{max}$ dose, then the exit dose at $D_{max}$ would be about 45% of the entrance dose. Hence it would be 45% of the 290 cGy that is 131 cGy. Then, if it were parallel opposed cross firing beams, then the total dose at $D_{max}$ is 421. As compared to the normal tissue maximum dose in my invention described below, this is a very high dose to normal tissue. The normal tissue maximum dose when treated by multiple pairs of parallel opposed beams as in my invention, the normal tissue maximum dose is calculated as 120 cGy when the target dose is 4,800 cGy in one embodiment and in another 60 cGy. Even if the normal tissue dose was 290 cGy at $D_{max}$ it is much higher than in my invention that is described below. Further more, the experimental 8 cross-fired beams in Example 3 of this patent seems to be sequential treatment. It has to be deduced from the specification of this patent. It is not specified in Example 3. Hence it also has no additive high dose rate at the isocentric tumor site. Hence it has poor radiobiological effectiveness for tumor cell kill and tumor control All Field Simultaneous Radiation Therapy The advantages of all filed simultaneous radiation therapy (AFSRT) and only few second duration sequential treatment of each field is described in the above cross-referenced non-provisional patent applications, provisional patent applications and disclosures. The AFSRT overcomes the disadvantages associated with lower daily radiation dose. It is described in this patent application and in the above referenced applications.

The Medical Accelerator systems described in Provisional Patent Application 60/872,117 of Nov. 30, 2006, Lethal and Sublethal Damage Repair Inhibiting Image Guided Simultaneous All Field Divergent and Pencil Beam Photon and Electron Radiation Therapy and Radiosurgery (10) facilitates actual beam on time to complete 200 cGy radiation therapy to all the setup fields in about 5 seconds and about 1,000 cGy radiosurgery in about 20 seconds.

Since a patient can hold breathing for more than 20 seconds, the breathing associated organ movement is not a hindrance to deliver accurate radiation therapy in such a short duration radiation therapy. It simplifies the single session high biological dose and dose rate and radiation therapy and radiosurgery to a patient with more precision and with limited patient fixation to the treatment table. It also improves the patient's comfort significantly.

In the textbook of Radiobiology for the Radiologist by Eric J. Hall the following statement on hyperthermia combined radiation therapy is included. "Although many experiments have been performed with cultured cells and with laboratory animals to investigate the interaction of heat and radiation, if hyperthermia is used in the clinic as an adjunct to radiation therapy, their effects are probably not interactive at all. Because of the daily doses used in conventional fractionated radiotherapy are small (2 Gy) and the levels of heating achieved are modest, the cytotoxicity of the heat and radiation are more probably independent but additive" (14, Page 510). In this invention, since single session hyperthermia combined with single session radiation therapy is used, the above disadvantages of hyperthermia combined with radiation therapy are eliminated.

The AFSRT's biological high dose and dose rate is the combined dose and dose rate of all converging simultaneous beams at isocenter when all the fields of a multiple field treatment setup is treated simultaneously. It kills more tumor cells than in conventional radiation therapy that is delivered by sub-fractionated daily-fractionated radiation therapy.

Here, the daily subfractionated radiation therapy is referred to as the daily-fractionated radiation therapy that is further subfractionated by treatment of each fields as one at a time. It is interrupted by the time required for each field's treatment-setup and treating and its elapsed time in between each field's treatment.

The radiation therapy system described in these applications is also capable of image guided combined single session simulation, block making, treatment planning and radiation therapy. It eliminates the protracted six to seven week long multiple session conventional radiation therapy.

The AFSRT uses multiple simultaneous beams, all converging simultaneously at the isocentric target volume to treat a tumor. The number of simultaneous beams, its dose rate and LET are the major factors that determine its radiobiological effectiveness (RBE). The multiple simultaneous beams additive dose rate is like the number of radioactive sources used that determines the dose rate of brachytherapy. In brachytherapy, the dose rate is used to calculate the total dose needed to cure a tumor. In brachytherapy, the total dose at dose rate of 0.357 Gy/h (35.7 cGy/h) for 7 days is 6,000 cGy. Its equivalent dose at the dose rate of 0.64 Gy/h (64 cGy/h) in 3 days is 4,600 cGy (15). Likewise, in AFSRT, the dose rate is also a function of the number of simultaneous beams and its biological dose rate. Each treatment head serves as a source. Like in brachytherapy, the total dose is varied according to this biological dose rate. In contrast to brachytherapy, the AFSRT is a single or fewer fraction super high dose rate method of radiation therapy.

Similar to brachytherapy with multiple radioactive sources, the Gamma Knife radiosurgery uses multiple 1 mm sized Cobalt-60 sources. These sources provide multiple simultaneous beams that converge at the focal point. Compared to the multiple simultaneous photon beams generated by multiple beam accelerators as in AFSRT, Gamma Knife's cobalt-60 beam has much poor qualities. Its dose rate is much poor and during the five year half-life of the cobalt-60, its dose rate further decreases. The dose rate has a significant effect on radiobiological effectiveness (RBE) in radiation therapy.

The Leksell Gamma Knife unit contains 201 small cobalt-60 sources. Before the half-life of the Cobalt-60 source, the combined effective dose rate at treatment distance from all the 201 cobalt-60 sources range from 125 to 170 cGy/min (16, 18). The median dose rate is 145 cGy. In AFSRT, the combined biological dose rate of all the simultaneous beams that converges at the isocenter depends on the number of beams and each beam's dose rate. In AFSRT, multiple accelerator based simultaneous beams converges at the isocenter. Depending on the number of beams and individual beam's machine dose rate, its biological dose rate at isocenter varies. For a 10×10-cm field size, 10-cm depth, 100-cm isocenter distance, and machine dose rate of 400 cGy/min, the biological dose rates for 2, 4, 6, 8 or 16 simultaneous beams of the AFSRT system is 579, 1,158, 1,737, 2,316 and 4,632 cGy/min respectively. It is further explained later under Fig. VIII. It renders completion of the treatment in a few seconds. Hence the uncertainties associated with the accurate coverage of the treatment volume due to organ movements during treatment are eliminated. A patient can hold the breath for a few seconds while the treatment is delivered. The few seconds only duration treatment can also be synchronized with the breathing movements of the patient. Its obvious radiobiological qualities are much more superior to that of cobalt-60 source based Gamma Knife's simultaneous beams. Its 201 simultaneous beams have an average dose rate of 145 cGy/min when its 4-mm helmet is used (18). Several small isocentric volumes within a target volume are treated with cobalt-60 Gamma Knife. Because of the 5.26-year half-life of cobalt-60, this dose rate would decrease to half of its initial dose rate. At 145 cGy/min, it would take about 10 or more min to deliver the radiosurgical dose of 1,000-1,500 cGy. This treatment time would double as the cobalt-60 source strength decays with its half-life. Hence, with 10-15 small treatment volumes within a target volume, the time taken to complete the radiation to the entire treatment volume is hours. It is not only cumbersome and time consuming but also radiobiologically very much inefficient. Compared to cobalt-60 Gamma Knife, the AFSRT system's superiority to deliver radiation therapy and radiosurgery in a few seconds is obvious.

In linear accelerator based radiosurgery, a single beam, multiple arc rotational treatment of the target volume is used. The target is treated with a single arc or multiple arc rotational isocenter plans or by multiple fixed fields (16). In the case of accelerator based arc rotational treatment, the single beam treats a portion of the treatment volume at any given time. In the case of multiple fixed field treatment, the single beam treats one field at a time. Both are interrupted, subfractionated treatment. Hence its radiobiological effectiveness is much inferior to that of AFSRT Radiosurgery with multiple simultaneous beams by the AFSRT method on the other hand offers many advantages than the radiosurgery with Gamma Knife or with single beam linear accelerator. The simultaneous beams of Gamma Knife has very low additive dose rate, in the range of 145-170 cGy, as compared to the additive dose rate of linear accelerator based AFSRT. Likewise, the single beam based radiosurgery with linear accelerator's dose rate is also very much inferior to that of the additive biological dose rate of AFSRT. In this instance, the dose rate at the target represents the single beam's dose rate at the target.

The simultaneous beams of AFSRT have much superior additive dose rate, that is its biological dose rate. A single accelerator 4 MV beam with dose rate of 400 cGy/min and the treatment parameters includes as an average tissue maximum ratio (TMR) 0.746, collimator scatter factor ($S_c$) 0.98, phantom scatter factor ($S_p$) 0.99, and the isocenter distance from the source 100 cm, then its dose rate at the isocenter is 289.5 cGy/min (26). Hence radiation therapy with such a single accelerator beam has 289.5 cGy/min at the isocentric target. Likewise, if the single beam's machine dose rate were 400 cGy/min, then the additive biological dose rates for 2, 4, 6, 8 or 16 simultaneous beams of AFSRT system is 579, 1,158, 1,737, 2,316 and 4,632 cGy/min respectively. This high dose rate of AFSRT contributes its significant radiobiological advantages as compared to that of Gamma Knife or single beam linear accelerator based radiosurgery.

The AFSRT's multiple simultaneous high-energy photon accelerators' beam helps to produce conformal intensity modulated treatment as a single session treatment with simultaneous multiple beams that covers the entire treatment volume. Each of the isocentric simultaneous beam's intensity is modulated to suite the three-dimensional volume of the target. Such conformal intensity modulated simultaneous treatment of a target tumor as in the AFSRT is not feasible with the Gamma Knife or with the conventional single beam accelerator based radiosurgery.

The radiobiological effectiveness of this new method of conformal treatment of a target volume with accelerator based simultaneous multiple beams with higher energy, higher dose rate and LET is much superior to that of radiosurgery with Gamma Knife or conventional linear accelerator based radiosurgery.

The linear energy transfer (LET) values vary for different sources of high-energy radiation beams. The LET is subdivided into track average and energy average. In track average, the amount of energy deposited in equal lengths is averaged. In energy average, the length of the track that contains equal amount of energy is calculated (19, page 114). For x-rays, both energy average and track average are similar. Both the track average and energy average for Cobalt-60 is 0.2 KeV/μ. Likewise, the track average and energy average for 250-kV x-rays is 2.0 KeV/μ, ten times higher than that for Co-60. Because of the lower LET of Cobalt-60 with 0.2 KeV/μ has about 10% less relative biological effectiveness (RBE) than that for 250 kV x-rays.

Unlike the x-ray beams, the proton beam's LET varies with energy. The 10 MeV proton has 4.7 KeV/μ energy averages while the energy average of 150 MeV proton is only 0.5 KeV/μ. Dice the x-rays, both the energy and track average for proton is the same. Hence 150 MeV protons are less effective in cell kill than 250 kV x-rays. For neutrons the track and energy average vary. The 14 MeV neutron's track average is 12 KeV/μ but its energy average is 100 KeV/μ. Because of this very high-energy average, neutron is much more effective in cell kill.

A single 250-kV x-ray beam with 2.0 KeV/μ. LET deposits its energy of 2.0 KeV/μ when it passes through the radiating tissue. Let us say that this 250-kV x-ray source is placed at 0-degree. When it is used to radiate the tissue, it's beam deposits 2.0 KeV/μ to the tissue. If a second similar x-ray source is placed at the opposite side say at 180-degree as parallel opposed to the first source and when the x-ray beams from both sources are allowed to passes through the same tissue simultaneously as parallel opposed beams, then the converging beam's energy deposited in the target tissue doubles. Now the total energy deposited in the target tissue has increased from 2 KeV/μ to 4.0 KeV/μ. If similar two simultaneous 250 KeV x-ray beams are made to strike the target tissue namely one from 90 degree and another from 270-degrees as another set of simultaneous parallel opposed beams, then all four simultaneous beam's converging total additive LET is 8 KeV/μ. These simultaneous beams improves the radiation quality and hence its RBE than if the target tissue were radiated with a single beam. If this four-field radiation therapy is delivered as sequentially, one field at a time as in present radiation therapy practice, then it is an interrupted subfractionated four field-four-beam therapy. Hence its energy average deposited in tissue by the single 250 kV x-ray beam is one fourth of the simultaneous four beam's energy deposited. Single 250 kV x-ray deposits one fourth of the energy as compared to four simultaneous 250 KeV beams, 2 KeV/μ.×4, that is the additive energy of 8.0 KeV/μ. If the number of simultaneous beams were increased from four to eight, or sixteen, then the converging additive energy deposited in tissue would increase to 16 KeV/μ and 32 KeV/μ respectively. Hence its RBE also increases. RBE depends on a number of factors, namely radiation quality LET, dose rate, dose, number of fractions, and the biological end point. Among them, the LET and dose rates are very important.

Cobalt-60 has poor LET and dose rate. Its LET is only 0.2 KeV/μ. However, by extrapolating the principles explained here on converging additive LET, multiple simultaneous beams could render additive dose rate and LET. This additive dose rate effect is used to achieve clinically usable dose rate in Gamma Knife radiosurgery. The Gamma Knife has 201 cobalt-60 sources. Each source is of 1 mm in size. The additive LET of 201 simultaneous cobalt 60 beams could be 201×0.2 KeV/μ is 40.2 KeV/μ. In spite of Gamma Knife's very poor dose rate and the Cobalt-60's short half life of 5.26 years, the treatment outcome for trigeminal neuralgia with Gamma Knife is reported as the same when the treatment was rendered during the early and late phase of Cobalt-60's half-life (4). During the later period of cobalt-60's half-life, its dose rate is reduced to half of its original value. Patients treated with Gamma knife during the later part of Cobalt-60's half-life had only about 50-cGy/min-dose rate at the isocenter. Still this low dose rate did not affect the outcome of trigeminal neuralgia (18). From the radiobiological and technical point of views, it is a very poor method of radiation therapy and radiosurgery. Still the treatment outcome with machine dose rate of 145 cGy and or 72.5 cGy is reported to be as the same (16). It is associated with Gamma Knife's 201 small Cobalt-60 sources and their 201 simultaneous beams, all converging into a small target simultaneously and their additive LET of 0.2×201 KeV/μ, 40.2 KeV/μ. However this additive LET effect of poor dose rate radiation with Gamma knife's 201 Cobalt-60 sources is not discussed or claimed anywhere before. Its additive dose rate is used for treatment with Gamma Knife.

AFSRT's simultaneous beams originate from medical accelerators. It is a much better radiating source than the Gamma Knife's cobalt-60 source. The AFSRT's simultaneous renders additive high dose rates and higher LET. Its superior radiobiology, namely its ability to inhibit the sublethal damage repair is obvious. It also completes the entire treatment to the treatment volume in seconds. Hence it eliminates the organ movement associated uncertainties on the conformal radiation therapy to a target volume.

The additive LET of simultaneous beams improves the radiation quality significantly. The LET of a machine which costs about 100 million-dollar and or higher MeV proton machine is just 0.5.0 KeV/μ, 16 times less than the additive LET of four simultaneous low cost 250 KeV x-ray beams. A higher energy simultaneous photon beam minimizes most of the disadvantages of 250-KeV machines. A radiation therapy machine with such high-energy simultaneous beams combined with radiation sensitizing single session hyperthermia renders a very effective radiation therapy system. A 4 or 6 MV medical accelerator beam also minimizes the penumbra effects of radiation to the target volume and to is surrounding normal tissue and critical organs.

Heat is a radiation sensitizer. Other actions of heat include enhancement of apotosis, induction of mitotic arrest or causing non-apototic cells to dye by necrosis. In fractionated hyperthermia, thermotolerance appears. It is due to synthesis of heat-shock proteins. Single fraction hyperthermia eliminates the thermotolerance. Hence single fraction radiation therapy combined with radiation sensitizing single fraction hyperthermia enhances the cytotoxicity of both radiation and hyperthermia.

Beams' Intensity Modulation

The intensity of multiple simultaneous beams from multiple treatment heads from a stationary machine or multiple simultaneous beams from multiple treatment heads of a rotating machine is modulated by beam flattening and filtering devices inserted into or out of the path of the beam exiting from each treatment head. The energy of such modulated beam is measured based upon its depth of penetration in tissue. In the absence of the flattening filter, more penetrating and hence higher energy pencil beam mode is obtained (22). When the flattening filter is inserted, lower penetrating and hence lower energy but broader divergent beam is obtained. With multiple treatment heads and each with a target, this combination of simultaneous divergent beam and parallel pencil beams modes for simultaneous varying energy radiation therapy is made possible. The divergent beam's energy and the parallel pencil beam's energy vary very much. Hence it provides a much better intensity modulated radiation therapy system than the intensity-modulated beam with multileaf collimator and similar devices. It facilitates conformal intensity modulated radiation therapy and radiosurgery based on 3-D configuration of tumor volume with millimeter precision. It is like scrapping of a tumor with a surgeon's knife without damaging the normal tissue.

Interaction Between Heat, Radiation and Chemotherapy

Many textbooks and scientific articles describe the synergic effects of hyperthermia, and radiation with or without chemotherapy. It is summarized in Chapter 28, Erick J. Hall's Textbook of Radiobiology for the Radiologist (14) They render independent but additive cytotoxicity. Hyperthermia and radiation therapy have different mechanism for cell killing; energy deposited from heat is thousand times greater than the energy deposited by radiation.

Hyperthermia is effective at S-phase of the cell cycle. It is also effective in cells that are nutritionally deficient, hypoxic and cells with high pH level. After hyperthermia, the cell death is by apoptosis. The sublethal damage repair after hyperthermia can take up to 120 to 160 hours. After the first treatment by hyperthermia, thermotolerance develops. The first hyperthermia treatment kills more cells than when it is repeated. Hence the first hyperthermia treatment above 43° C. has a steeper cell survival curve than that for the x-ray radiation treatment. Repeated hyperthermia treatment however has a shallower cell survival curve. It is because of the development of thermotolerance after the first treatment. Hyperthermia sensitizes the cell to radiation by inhibition of the cell's ability to repair the sublethal and the potentially lethal damage for longer period. Hence the synergetic effects of hyperthermia and radiation.

Thermotolerance and heat-shock protein synthesis after the first hyperthermia treatment makes repeated hyperthermia treatment less effective. After the first hyperthermia treatment, the thermotolerance starts to develop possible by starting the synthesis of heat-shock protein. After the first treatment, it may take about 1 to two days for thermotolerance to reach its maximum. This thermotolerance persists for about two weeks before it decays completely. Because of this rapid thermotolerance development and lasts for a longer time, it is recommended to use only one hyperthermia treatment or at the most two.

Radiation is effective at $G_2$ and M phase of the cell cycle. It is less effective to $G_1$ and S-phase cells. Hypoxia also minimizes radiation effectiveness. The sublethal damage repair after radiation therapy is a lot shorter time, about a few hours only which is the basis for the time interval of 6 hours between treatments when daily hyperfractionated radiation therapy is rendered. Because of the rapid sublethal damage repair after daily-fractionated dose of 200 cGy, the cell survival curve has a larger shoulder and a shallow slope. Higher dose and dose rate radiation therapy can improve cell kill by radiation and the cell survival curve with steeper slope. After radiation therapy, cell death occurs when cells attempt to undergo the complex process of cell division.

Heat inhibits repair of single strand breaks and chromosome aberrations induced by radiation. It is due to sublethal damage repair and the potentially lethal damage repair inhibition by hyperthermia. Repair of sublethal damage does not occur if hyperthermia is applied during radiation.

In present clinical practice of combined hyperthermia and radiation therapy do not provide the same results that are shown in experiments with cultured cells and with laboratory animals. Those experiments were done with long-term exposure of much higher temperature and much higher dose radiation exposure. Clinically, such treatment of the patients is not feasible. The clinically possible modest heating combined with modest daily-fractionated radiation dose of 180 to 200 cGy cannot reproduce the same results as those observed in experiments with cell cultures and laboratory animals. With the present available technologies it is impossible to treat a patient with combined single higher dose radiation ranging from 500 to 2,000 cGy and temperature at 43° C. and above. Hence the laboratory results of hyperthermia alone or combined with radiation and or chemotherapy is almost irrelevant in clinical practice. By the present methods of combined hyperthermia and radiation and or with chemotherapy, only their modest potential benefit for cancer treatment is realized. The clinically observed modest tumor control by such combined treatment is more likely independent of each other and most likely additive.

The all field simultaneous radiation therapy system described by this inventor in previously referred patent applications can deliver high radiosurgical radiation dose with biological high dose rate in a few seconds. The Medical Accelerator System that treats each treatment field sequentially completes higher dose radiation, 1,000 cGy in about 40 seconds. This method of radiation therapy minimizes the toxic effects of high dose and dose rate radiation. It is discussed extensively in those provisional and regular patent applications. Because of this high dose and super-high biological dose rate, it inhibits most of the sublethal and potentially lethal damage repair. Its higher relative radiobiological effectiveness (RBE) is closer to that of high LET radiation. Its cell survival curves are steeper, approaching close to that of high LET radiation. Hence it is a more suitable radiation therapy delivery system that can be used with hyperthermia.

Using the AFSRT for single fraction, single isodose radiosurgical dose radiation therapy with high biological dose rate and higher RBE further enhances the first hyperthermia treatment's cell kill as evidenced by its first steeper portion of the cell survival curves.

In this instance, repeated daily-fractionated radiation therapy is not needed. Likewise, there is no need for repeated hyperthermia treatments. It thus overcome the lower dose associated lesser effectiveness of radiation and the thermotolerance of hyperthermia. The combined high dose and biological dose rate radiation to the tumor with lesser toxicity to normal tissue and a single hyperthermia and radiation treatment overcome the sublethal and potentially lethal damage repair of lower dose radiation leading to higher effective RBE and tumor cure and control with lesser toxicity. Such combined radiation therapy and hyperthermia is not feasible with present systems.

Hyperthermia is known to enhance the effectiveness of cell kill that renders steeper cell survival curves than when chemotherapeutic agents alone are used. The chemotherapeutic agents so tested include bleomycin, cisplatin, doxorubicin, and a number of other clinically used agent (14). Like with the radiation, hyperthermia is synergistically effective with chemotherapeutic agents. It enhances its effectiveness at cellular level. The patient tolerates clinically feasible modest temperature hyperthermia much better. While it is not very effective in cell kill, it initiates the thermotolerance possibly by synthesis of heat-shock-protein, which seems to be the mediator for inhibiting the sublethal damage repair after radiation therapy and chemotherapy. Combined higher dose and super-high biological dose rate radiation with low dose chemotherapy will render the tumor tissue more susceptible to such combined treatment.

Based upon the tumor site hyperthermia to the tumor is delivered either as superficial, interstitial or as deeper site hyperthermia by radio frequency induced hyperthermia or by deeper microwave thermal hyperthermia. About 40 minutes to an hour hyperthermia treatment might be sufficient when it is combined with radiation. Hyperthermia machines are readily available commercially. There are even MRI interfaced commercial hyperthermia units for MRI monitored delivery of hyperthermia to deep-seated organs.

In the provisional patent application 60/927,622, "Single Session Interactive Image Guided Simulation, Field Shaping, Treatment Planning and Ultra Short Duration Super-High Biological Dose Rate All Filed Simultaneous or Sequential Radiation Therapy and Radiosurgery" filed on May 3, 2007 (12) and its non-provisional patent application Ser. No. 12/151,014 filed on May 3, 2008, (13) the image guided radiosurgery is described. It has much similarity to image guided surgery. In combined image guided surgery and radiosurgery, local hyperthermia to the tumor site is applied as radio frequency induced interstitial hyperthermia or as microwave hyperthermia to well defined treatment portals. The single session higher dose, super high biological dose rate radiation therapy and hyperthermia to the tumor that is surgically defined improves this treatment's effectiveness significantly.

Hall under Human Application of Hyperthermia cites the beneficial effects of hyperthermia induced by Coley's bacterial toxin. Dr. William B Coley described beneficial effect of hyperthermia induced by bacterial infection in 1891 (14). Citing Dr. Coley's bacterial toxin induced fever therapy's beneficial effects in a 1996 article in the Internet," Cancer Guide Alternative and Complementary Therapies", by Matti Narkia (20) summarizes it as an effective treatment for even inoperable advanced carcinomas.

The 5 year survival after fever therapy with Coley's toxin is reported to render 79% of inoperable giant cell carcinoma of the bone, 65% of inoperable carcinoma of the breast, 67% of Hodgkin's disease, 67% of inoperable carcinoma of the breast and 60% of the inoperable malignant melanoma (20). When it is compared to the modern hyperthermia combined with radiation therapy for advanced tumors, it is a very impressive result for treatment with Coley's toxin. The radio frequency or microwave power induced hyperthermia combined with radiation is reported to have 68.2% control of breast cancer and 51% overall survival at three years for patients with carcinomas of the cervix and vagina. Patients with cervical and vaginal cancer and who were not treated with hyperthermia combined with radiation had only 27% three-year survival Similar encouraging results were observed for patients with carcinoma of the bladder, prostate, rectum and children with malignant soft tissue sarcoma. Similar results were also reported by others (21, 23).

Radio frequency or microwave power induced hyperthermia combined with small doses of immune stimulant hyperthermia like those with Coley's toxin and AFSRT with high dose and super-high biological dose rate radiation will further enhance the effectiveness of radiation therapy combined with hyperthermia. Using the recall phenomenon, immune stimulants could be used as a form of radiogenetic treatment that enhances the radiation sensitivity of the tumor tissue. After priming the tumor tissue with a bacterial toxin and then giving an intravenous injection of the same bacterial toxin will elicit the necrosis factor. By increasing the selective radiosensitivity of the tumor tissue, much lesser radiation dose might be needed to treat a tumor. It would enhance tumor cure and control while minimizing the toxic effects of radiation.

Image Guided Surgery Combined with Radiation Therapy

Image guided surgery is now well established. The MV-CT and MRI images are used for online dynamic interactive viewing of the surface and internal anatomy as 3-D and 4-D VR CT or 3-D and 4-D VR MRI images. They are used for image guided surgery (24) and radiation therapy. When the Medical Accelerator System is combined with CT imaging only, such processed CT imaging is used for interactive single session combined simulation, block making and treatment planning. When the Medical Accelerator System is equipped with both CT and MRI imaging capabilities, CT and MRI imaging are used for online image guided simulation; block making, and treatment planning. Generally, the CT-MRI fused images are used for treatment planning. It overcomes the difficulties associated with MRI's non-correlating pixel intensities between bone-air interfaces as with MRI of the sinuses. It also eliminates the need to introduce an endorectal probe for MRI of the prostate. The fused CT-MRI image provides sufficient imaging details of the prostate for the treatment planning.

MRI also facilitates functional imaging by magnetic resonance spectroscopic imaging (MRSI). The CT combined with MRI and functional imaging the MRSI are also used for online dynamic interactive views of the surface and internal anatomy of the treating tumor volume. The tumor volume is visualized as 3-D and 4-D VR images on a stereoscopic screen and as 2-D images on a 2-D monitor. It helps to improve precise simulation, block making and treatment planning and to improve the quality of radiation therapy. It is further detailed in the section on method of operation.

BRIEF DESCRIPTION OF THE DRAWINGS

FIG. 1 is an illustration of 6 accelerators configured with an open magnet for combined MV-CT and MRI image guided radiation therapy and radiosurgery with six transverse plane coplanar beams.

FIG. 2 Shows non-coplanar beams from accelerator treatment heads that are arranged circularly around the imaging and treatment table to render non-coplanar beams and the open magnet for image guided all fields' simultaneous radiation therapy and radiosurgery.

FIG. 3 L 1 Demonstrates eight parallel opposing, four pairs of opposing treatment heads each with a single isotopic sources like cobalt-60 and eight such treatment heads arranged in a circle with their simultaneous beams converging at the isocenter for γ-ray teletherapy. The two segments of a split magnet are moved above the ground for MRI guided simultaneous eight beams, γ-ray teletherapy.

FIG. 3 L 2 Demonstrates eight parallel opposing, four pairs of opposing treatment beads each with five isotopic sources like cobalt-60 and eight such treatment heads arranged in a circle with their simultaneous beams converging at the isocenter for about 24 seconds duration, breathing synchronized, high-dose rate γ-ray teletherapy and radiosurgery but with less than 20 cGy $^{60}$Co $d_{max}$ dose. The two segments of a split magnet are moved above the ground for MRI guided simultaneous eight beams, γ-ray teletherapy.

FIG. 3 M Demonstrates sixteen parallel opposing, eight pairs of opposing treatment heads each with a single isotopic sources like cobalt-60 and sixteen such treatment heads arranged in a circle with their simultaneous beams converging at the isocenter for γ-ray teletherapy. The two segments of a split magnet are moved above the ground for MRI guided simultaneous eight beams, γ-ray teletherapy.

FIG. 3 N 1 demonstrates eight parallel opposing treatment heads each with five isotopic sources like cobalt-60 and eight such treatment heads arranged in a circle with their simultaneous parallel beams providing an array of cross firing simultaneous beams at the isocenter for about 12 seconds duration, breathing synchronized, high-dose rate γ-ray teletherapy and radiosurgery but with less than 20 cGy $^{60}$Co $d_{max}$ dose from each beam. The two segments of a split magnet that are moved to above the ground for MRI guided simultaneous eight beams γ-ray teletherapy.

FIG. 3 N 2 Demonstrates sixteen parallel opposing treatment heads, each with five isotopic sources like cobalt-60 and sixteen such treatment heads arranged in a circle with their simultaneous parallel beams providing an array of cross firing simultaneous beams at the isocenter for about 6 seconds duration, breathing synchronized, high-dose rate γ-ray teletherapy and radiosurgery but with less than 10 cGy $^{60}$Co $d_{max}$ dose from each beam. The two segments of a split magnet that are moved to above the ground for MRI guided simultaneous eight beams, γ-ray teletherapy.

FIG. 3 N 3: Demonstrates eight parallel opposing treatment heads, four with five isotopic sources like cobalt-60 in each treatment head and four with single Linac x-ray beam. Eight such treatment heads are arranged in a circle with their simultaneous parallel beams providing an array of cross firing simultaneous beams at the isocenter for combined γ-ray and Linac x-ray beam for radiosurgery and radiation therapy. The two segments of a split magnet are also shown moved to above the ground for MRI guided simultaneous eight beams, combined Linac x-ray and γ-ray radiation therapy.

REFERENCE NUMERALS

Figure 3A:
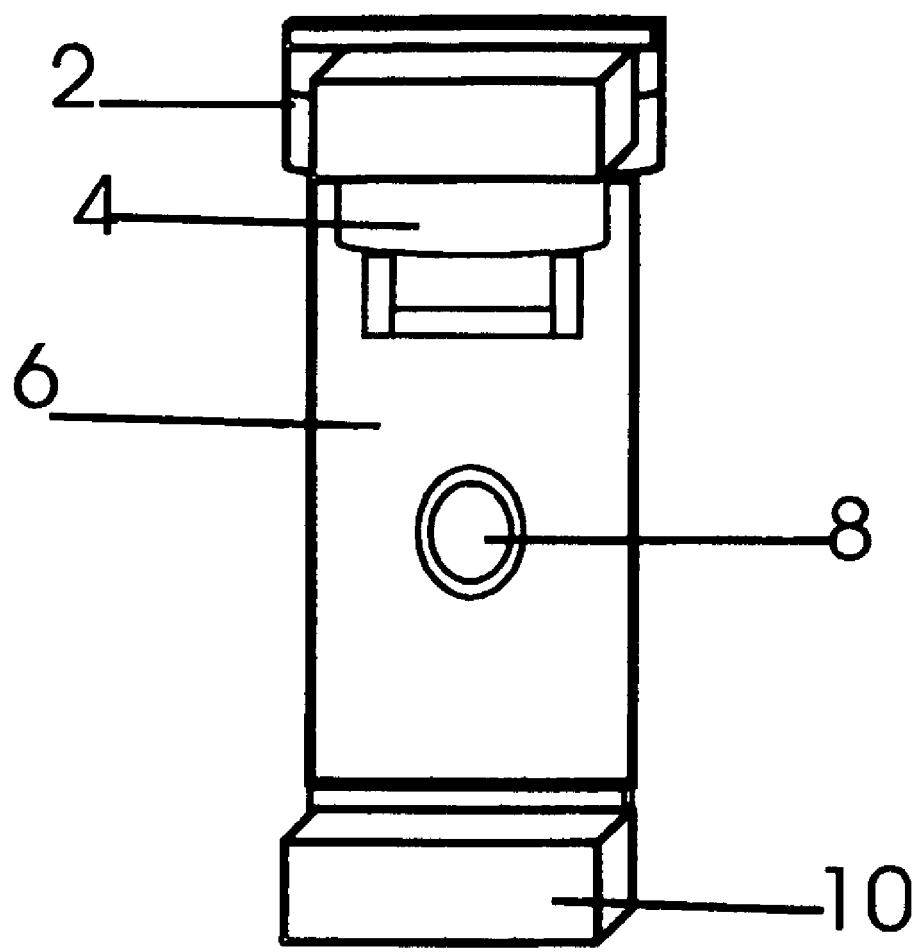
FIG. 3A Is an illustration of a conventional medical accelerator with its rotating gantry and the counter weight FIG. 3B Shows two conventional medical accelerators mounted on to a common rotating gantry system for two field simultaneous rotational radiation therapy and radiosurgery or two-field simultaneous radiation therapy or radiosurgery with or without hyperthermia.

2 Treatmenthead
4 Collimation and accessory holder
6 Gantry
8 Protractor
10 Counterweight—beam shield
66 Isocenter
172 Patient
174 Treatment table
282 Open magnet segment one
283 Lifting and retracting piston
284 Open magnet segment two
285 Lifting and retracting piston
287 Floor
290 Ceiling
289 Non-rotating accessory holding cabinet
302 Tumor
305 Isocentric additive biological dose rate and LET
309 Circular collimator
314 Accelerator in non-coplanar plane
316 Converging non-coplanar 7 beams
318 Circular planes
332SF Surviving fraction for single session high dose and dose rate radiation
334$D_1$ Surviving fraction for radiation therapy alone
336$D_1$ RT+HPT, Cell survival curve, high dose and dose rate radiation plus single session hyperthermia
338RT Single session radiation dose 340SF Surviving fraction for single session hyperthermia plus radiation
342HPT Surviving fraction for first session hyperthermia
344$D_1$ RT+HPT Surviving fraction for first session hyperthermia plus radiation
346$D_1$ Survival curve for first session hyperthermia
346$D_2$ Survival curve for second session hyperthermia
346$D_3$ Survival curve for third session hyperthermia
352 HTP-Treatment time: Hyperthermia treatment time
353 Track energy average)?
354 Single beam with single beam's dose rate and LET
355 Cobalt-60 single beam with single beam's dose rate and LET
356 Simultaneously converging single beam 1
358 Simultaneously converging single beam 2
360 Simultaneously converging single beam 3
362 Simultaneously converging single beam 4
364 Treatment head at 0-degree
380 Cobalt-60 housing treatment head
381 Five cobalt-60 source in one treatment head
382 Converging single cobalt-60 beam
384 Combined simultaneously converging cobalt-60 beam at isocenter
386 Circular radiation shield
388 Small cobalt-60 sources converging beam
390 Circular rotating gantry
392 Converging single source cobalt-60 beam
394 Simultaneous cobalt-60 and accelerator beam at isocenter
396 Single Linac x-ray beam
398 Linac treatment head

DESCRIPTION OF THE PREFERRED EMBODIMENTS

FIG. 1 Is an illustration of 6 accelerators configured with an open magnet for combined MV-CT and MRI image guided radiation therapy and radiosurgery with six transverse plane coplanar beams. The accelerator and its components are manufactured from non-magnetic metals like tungsten, lead and other non-magnetic metallic alloys. The accelerators 2 with the accessory holder 4 are configured at 0.45, 135, 180, 225, and 315 degree angles. An open magnet's two segments are placed in between the table on which the patient is placed during imaging. The open segment one 282 and the open magnet segment two 284 placed in between is a conventional open magnet MRI but adapted to work together with the medical accelerator and configured to fit with the accelerator arrangements. The accelerator and the segments of the magnet are in a transverse plane. The lifting and retracting pistons 283 and 285 that are attached to the magnet segments are used to bring the magnet in imaging position close to the patient 172. After imaging and when the magnet segments are not in use, they are retracted away from the accelerator room. Retracted magnet segments are kept below the floor 287 as shown in Fig III D, III E and Fig. IV H. Both MV-CT and MRI combined imaging are used for image guided radiation therapy and radiosurgery. With a strong magnet and its strong magnetic field the functional imaging by magnetic resonance spectroscopic imaging, MRSI is also made feasible. The shielding is made of non-magnetic material. In this instance, it is made of lead. The lead vault shielding 138 surrounds the accelerator and the The treatment heads, the shielding and other structures are built from non-magnetic material or they are encased in non-magnetic materials.

FIG. 2 Shows non-coplanar beams from accelerator 314 in non-coplanar plane are arranged circularly around the imaging and treatment table to render non-coplanar beams and the open magnet for image guided all fields' simultaneous radiation therapy and radiosurgery. The converging non-coplanar beams 316 is shown as focused onto the tumor 302. The imaging and treatment table 174 A is inserted at the center of thus configured radiation therapy machine. The open magnet segment-one, 282 is shown attached to the ceiling and the open magnet segment-two, 284 is shown attached to the ground. The lifting and retracting pistons 283 and 285 are attached to the magnet segments. They are used to bring the magnet in imaging position close to the imaging and treatment table 174. When the magnet segments are not in use for imaging, they are retracted away from the accelerator room. Retracted magnet segments are kept below the floor 287 and or above the ceiling 290. A sliding wedge in the ceiling lead shied allows moving the magnet up or down. The circular planes 318 illustrate the position of the accelerator heads around the imaging and treatment table 174 A. Both MV-CT and MRI combined imaging are used for image guided radiation therapy and radiosurgery. With a strong magnet and its strong magnetic field the functional imaging by magnetic resonance spectroscopic imaging, MRSI is also made feasible. The entire unit is placed within a lead vault shielding 138. The treatment heads, the shielding and other structures are built from non-magnetic material or they are encased in non-magnetic materials.

FIG. 3: shows a conventional medical accelerator with its rotating gantry and the counter weight is shown. Its treatment head 2, collimator and accessory holder 4, gantry 6, protractor 8 and the counterweight—beam shield 10 are modified and adapted to use in this invention. Such a conventional medical accelerator's basic structure is converted into a two beam medical accelerator by mounting additional treatment head and accelerator accessories in the space occupied by the counterweight-beam shield 10 as shown in FIG. 3B.

Figure 3B:
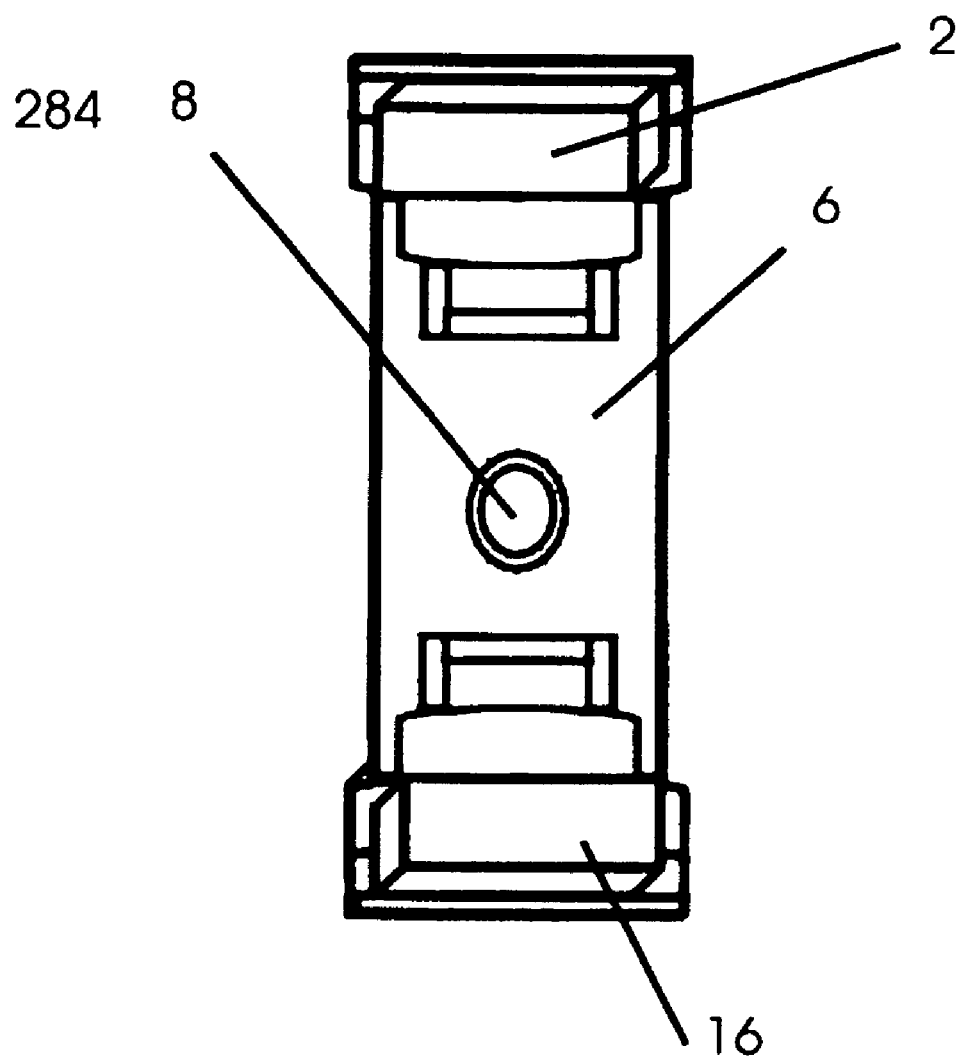
FIG. 3C Shows two conventional medical accelerators mounted on to a common rotating gantry and two movable segments of a split magnet that are moved to above the ground imaging position for MRI and MRSI of the patient for image guided two beam simultaneous rotational or two field simultaneous radiation therapy and radiosurgery or combined image guided surgery and radiosurgery or hyperthermia combined radiation therapy FIG. 3D Shows two conventional medical accelerators mounted on to a common rotating gantry and two movable segments of a split magnet that are moved to below the ground to free the treatment room from the magnet to rotate the gantry with the accelerator without any interference FIG. 3E Shows two conventional medical accelerators mounted on to a common rotating gantry rotated to the horizontal position. The two movable segments of a split magnet are moved to below the ground. It frees the treatment room from the magnet and facilitates the rotation of the gantry with the accelerator without interference from the MRI FIG. 3F Demonstrates four medical accelerators adapted for simultaneous four-beam radiosurgery and they are mounted on to two rotating gantries, one accelerator at each end of each gantry and the two movable segments of a split magnet that are moved to below the ground to free the treatment room from the magnet and to rotate the gantry with the accelerators without any interference FIG. 3G Illustrates four narrow simultaneous beams from all four medical accelerators shown in FIG. 3G as they make a simultaneous 90-degree arc rotation. Each accelerator contributes one segments of the beam that converges at the isocenter. As the accelerators rotate, the simultaneous four narrow beam segments treat four narrow segments of the tumor at the isocenter at a time. Combined, all such simultaneous segments of the beam from the simultaneously rotating four-accelerators make a full circle high dose region in the target tumor at the isocenter.
FIG. 3H illustrates two narrow simultaneous beams from only two of the four adjacent medical accelerators, accelerator 1A at 270° and accelerator 2A at 0° as shown in FIG. 3H. Each segment of their simultaneous narrow beams converges at the isocenter as they make a 90°-arc rotation. As the accelerators rotate, the simultaneous two narrow beam segments treat two narrow segments of the tumor at the isocenter at a time. Combined, all such simultaneous segments of the beam from the simultaneously rotating two-accelerator make a half circle high dose region in the target tumor at the isocenter.
FIG. 3 I Illustrates theoretical 201 simultaneous microbeams from 201 radioactive sources all arranged in a circle and all those micro-beams converging at its central focal point. It is to illustrate the concept of additive dose rate of such converging beams at the isocentric focal point like the additive dose rate of brachytherapy and Gamma Knife FIG. 3 J Illustrates theoretical 201 simultaneous microbeams from 201 radioactive sources all arranged in a half-circle hemisphere and all the micro-beams converging at its central focal point. It is also to illustrate the concept of additive dose rate of such converging beams at the isocentric focal point like the additive dose rate of brachytherapy and Gamma Knife FIG. 3 K Demonstrates two medical accelerators adapted for simultaneous two-beam radiation therapy and radiosurgery. The accelerators are mounted on to one rotating gantry, one accelerator at each end of the gantry. The two movable segments of a split magnet that are moved to below the ground to free the treatment room from the magnet. It facilitates the rotation of the gantry with the accelerators without interference from the MRI.

FIG. 3B shows two conventional medical accelerators mounted on to a common rotating gantry system for two field simultaneous rotational radiation therapy and radiosurgery or two-field simultaneous radiation therapy or radiosurgery with or without or hyperthermia. The accelerators are mounted on to a fully rotating gantry 6. The counterweight-beam shield 10 is replaced with a second accelerator or a cobalt-60 source 16. The isocenter distance to a patient or to a phantom on the treatment table is 100 cm. It is a simpler configuration two-beam model Medical Accelerator system of this invention. It differs much from other Medical Accelerator models of this invention. It also differs from the narrow two treatment heads holding gantry system that is incorporated onto more than two simultaneous beam Medical Accelerators. In this instance, like in a conventional Medical Accelerator, each accelerator has its own wave guide, electron gun, bending magnet, cooling system, collimation, accessory holder, dose monitors. It is either made to share the microwave power from a common klystron or from a magnetron or separate magnetrons for the microwave power. It functions is similar to a conventional single treatment head medical accelerator but in this instance, with two beams coming towards the isocenter from two treatment heads and its ability to deliver rotational treatment, it serves as an eliminatory Medical Accelerator that can treat a tumor with simultaneous exposure from multiple angles. Smaller tumors in the chest like those of early stage lung cancer, esophageal tumors, abdominal cancers like those of the bile duct, pancreas, colon and small pelvic tumors like those of small bladder, rectum, prostate, ovary and the uterine all can be treated with this rotating two-beam Medical Accelerator system simultaneously. However, it is a much-limited machine as compared to other models of this invention. The rotational treatments with two simultaneous beams, there are no inter-field interruption and hence no subfractionated daily fractionated radiation therapy. By making one accelerator's treatmenthead to deliver pencil beam, some of the features of the other models of this invention is obtained with this simpler Medical Accelerator system as well Field shaping without MLC as described in the section on Method of Operation is also applicable for this model but without the aid of online imaging system. With combined divergent and pencil beam capability, it can also deliver single isodose radiosurgery. This system delivers radiation therapy without inter-field interruptions. It treats a tumor with much more improved radiobio logical effectiveness than the present conventional single beam Medical Accelerators.

Figure 3C:
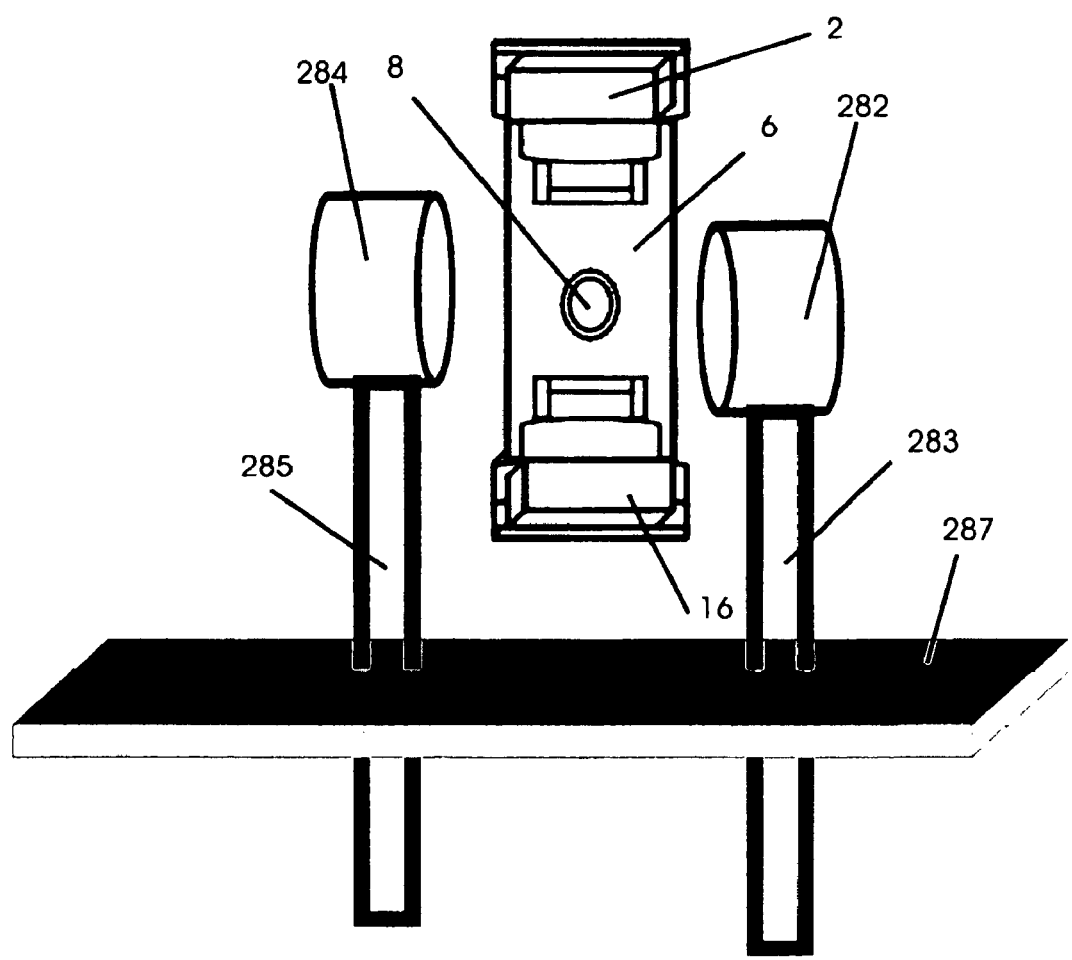

FIG. 3C Shows two conventional medical accelerators mounted on to a common rotating gantry and two movable segments of a split magnet that are moved to above the ground imaging position for MRI and MRSI of the patient for image guided two beam simultaneous rotational or two field simultaneous radiation therapy and radiosurgery or combined image guided surgery and radiosurgery or hyperthermia combined radiation therapy. It functions as a two beam simultaneous treatment Medical Accelerator system as described under FIG. 3B but as MRI-image guided radiation therapy system. The treatment heads, the shielding and other structures are built from non-magnetic material or they are encased in non-magnetic materials.

Figure 3D:
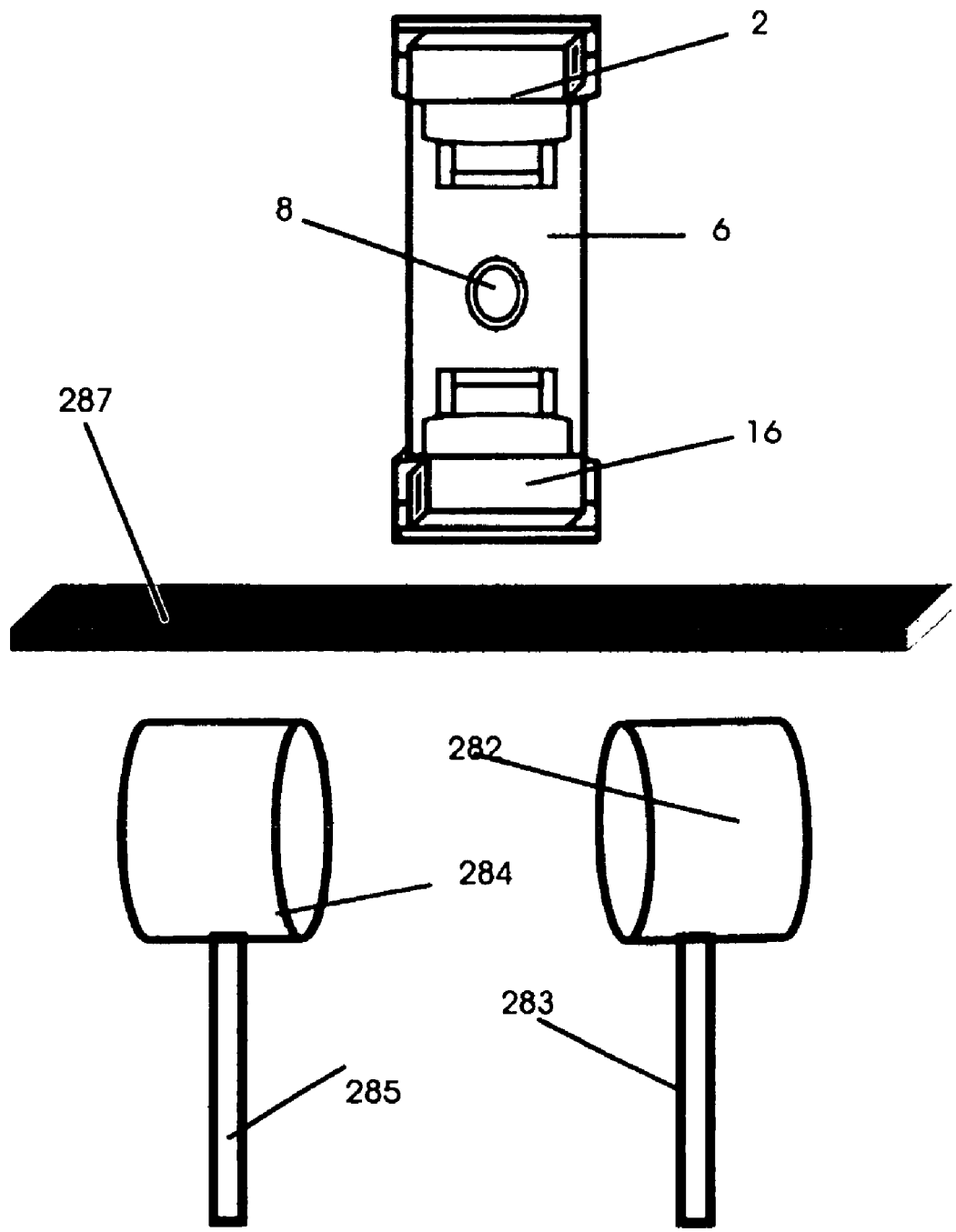

As shown in FIG. 3D, the open magnet segment one 282 and the open magnet segment two 284 are moved from below the ground with the aid of a motor driven lifting and retrieving piston attached to the magnet segments. The lifting and retracting piston 283 lifts or retracts the open magnet one 282. The lifting and retracting piston 285 lifts or retracts the open magnet one 284. The gantry 6 with the two accelerators and the treatmentheads 2 and 16 with the collimation and accessory holder 4 are in 0-degree position and the protractor 8 is also shown in FIG. 3C. The magnet segments are lifted from below the ground underneath the accelerator room and is brought closer to the gantry for MRI of a patient placed in treatment position on the treatment table (table not shown in this FIG. 3 C). When the MRI and MRSI imaging is completed the magnet segments are retracted to bring them below the ground floor 287. It is illustrated in FIG. 3D, FIG. 3E and FIG. 3F. The 2 beam simultaneous rotational or simultaneous two beam, two field radiation therapy is delivered with combined divergent and or pencil beam. For pencil beam, the flattening filter is moved away from the path of the beam emerging from the accelerator. Field shaping is with tungsten powder paste or with multileaf collimator. It also enables online single session MRI image guided simulation, field-shaping block making and treatment planning. It is described in detail in the provisional patent US Provisional and Non-Provisional Patent Applications 60/927,622, filing date May 3, 2007 and its non-provisional application Ser. No. 12/151, 014, filing date May 3, 2008 "Single Session Interactive Image Guided Simulation, Field Shaping, Treatment Planning and Ultra Short Duration Super-High Biological Dose and Dose Rate All Field Simultaneous or Sequential Radiation Therapy and Radiosurgery (13)

FIG. 3D Shows two conventional medical accelerators mounted on to a common rotating gantry and two movable segments of a split magnet that are moved to below the ground to free the treatment room from the magnet to rotate the gantry with the accelerator without any interference. As described in FIG. 3C after the MRI is done, the open magnets segment one 282 and the open magnet segments 284 are retrieved to below the floor 287. It enables the free rotation of the gantry like in a conventional medical accelerator. The gantry rotation drive is located in the non-rotating accessory holding cabinet 289. It is illustrated in FIG. 3E. The treatment heads, the shielding and other structures are built from non-magnetic material or they are encased in non-magnetic materials.

If it were four fields, single session, 800-cGy-radiation therapy or radiosurgery, with two simultaneous beams, the dose delivered by each beam to the tumor at the isocenter 66 is 400 cGy. A beam with the dose rate of 800 cGy/min and with the following treatment parameters, average tissue maximum ratio (TMR) 0.746, collimator scatter factor ($S_c$) 0.98, phantom scatter factor ($S_p$) 0.99, and the isocenter distance from the source 100 cm has 579 cGy at the isocenter. Two such beam's additive biological dose rate at the isocenter is 579×2 is 1,158 cGy. Hence, the time to deliver 4.00 cGy to the isocenter by each beam is $400/1,158$ min or 0.3454 min or 20.7254 seconds. Since the first two fields are treated with two simultaneous beams its additive dose to the tumor at the isocenter 66 is 800 cGy. This combined 800 cGy to the tumor is delivered in 20.7254 seconds. This short duration beam on time enables breathing synchronized precision radiation therapy much easier.

FIG. 3E Shows two conventional medical accelerators mounted on to a common rotating gantry as rotated to the horizontal position. The two movable segments of a split magnet are moved to below the ground. It frees the treatment room from the magnet and facilitates the rotation the gantry with the accelerator without interference from the MRI. As described under FIG. 3D, the open magnet segment 282 and the open magnet segment 284 are retrieved to below the ground 287. The gantry 6 with two accelerators and the treatment heads 2 and 16 is rotated and brought to horizontal position. The treatment heads, the shielding and other structures are built from non-magnetic material or they are encased in non-magnetic materials.

FIG. 3F demonstrates four medical accelerators adapted for simultaneous four-beam radiosurgery. They are mounted on to two rotating gantries, one accelerator at each ends of each gantry. Two movable segments of a split magnet that are moved to below the ground to free the treatment room from the magnet is also shown. It helps to rotate the gantry with the accelerators without any interference. The perpendicular and horizontal gantry hold one accelerator treatment head 2, at each ends with a circular collimator 309 which reaches close to the patient when a patient is placed in treatment position on the treatment table (not shown). The mm-sized accelerator source, low beam energy of 2-6 MV and the circular collimator 309 minimizes the penumbra of the beam at the target. The narrow beam from each accelerator is collimated with the circular collimator 309 as it emerges from it. For stationary treatment mode, the collimation for each beam is carved out at the time of the single session simulation and treatment with tungsten powder mixture. It is described below under methods of operation. Other means of beam collimation used includes micro-multileaf collimation. Simultaneously converging single beam 1, 356, and the simultaneously converging single beam 2, 358, from the perpendicular gantry's accelerator treatmentheads 2 converge at the isocenter 66. Likewise simultaneously converging single beam 3, 360 and simultaneously converging single beam 4, 362 from the horizontal gantry's two accelerator treatmentheads 2 converges at the isocenter 66. It renders four simultaneous beams, all converging at the isocenter 66. These four simultaneous beams, all converging at the isocenter 66 renders the isocentric additive biological dose rate and LET 305. As described before, such simultaneous beam radiosurgery has many unique radiobiological advantages. If needed, selectively any of the four beams from any of the four accelerators is not activated. It helps conformal treatment of the target tissue with lesser or no radiation to the surrounding normal tissue and critical organs. It is obvious that the positions of the perpendicular and horizontal gantries as shown in FIG. 3F would change as they rotate around the isocenter 66. The arrow indicates the direction of the rotation. The two movable segments of a split magnet are moved to below the ground. It frees the treatment room from the magnet and enables to rotate the gantry with the accelerator without any interference. As described under FIG. 3D the open magnet segment 282 and the open magnet segment 284 are retrieved to below the ground 287. The treatmentheads, the shielding and other structures are built from non-magnetic material or they are encased in non-magnetic materials.

If it were four fields, single session, 800-cGy-radiation therapy or radiosurgery, with four simultaneous beams, the dose delivered by each beam to the tumor at the isocenter 66 is 200 cGy. The dose rate at isocenter, $D_{iso}=D_0 \times S_c \times S_p \times$Average TMR (26, p 217). A beam with the $D_0$ dose rate of 400 cGy/min and with the following treatment parameters, average tissue maximum ratio (TMR) 0.746, collimator scatter factor ($S_c$) 0.98, phantom scatter factor ($S_p$) 0.99, has the $D_{iso}$ of 400×0.98×0.99×0.746 cGy that is 289.5 cGy, which is 289.5 cGy dose rate at the isocenter. Four such beam's additive biological dose rate at the isocenter is 289.5×4 is 1,158 cGy. Hence the time to deliver 200 cGy to the isocenter by each beam is $^{200}/_{1,158}$ min or 0.1121 min or 10.362 seconds. Since all the four fields are treated simultaneously these four beams' additive dose to the tumor at the isocenter 66 is 800 cGy. This combined 800 cGy to the tumor is delivered in 10.362 seconds. This short duration beam on time enables breathing synchronized precision radiation therapy much easier.

The given dose calculation for a single session rotational radiation therapy with four simultaneous beams could be analyzed as the following. The $D_{iso}$, from each accelerator is shown as 289.5 cGy. The $D_{iso}$ for four simultaneous beams from four accelerators is 289.5×4 is 1,158 cGy. The dose delivered at isocenter from each accelerator is 200 cGy. Hence the beam on time for each beam is $^{200}/_{1,158}$ is 0.1727 min or 10.362 seconds. This short duration beam on time enables breathing synchronized precision arc radiation therapy much easier. A patient can hold breathing during this time. Each of the four accelerators is placed at 90 degrees apart. Hence when each accelerator makes a 90°-arc rotation, the combined rotation of all the four accelerators is 90×4 is 360°. The operating technical limitation in arc treatment limits the arc to dose ratio. The dose cannot be more than five times the arc in degrees. This formula allows about 450-cGy maximum dose rate for each accelerator when they are used in arc treatment.

Figure 3G:
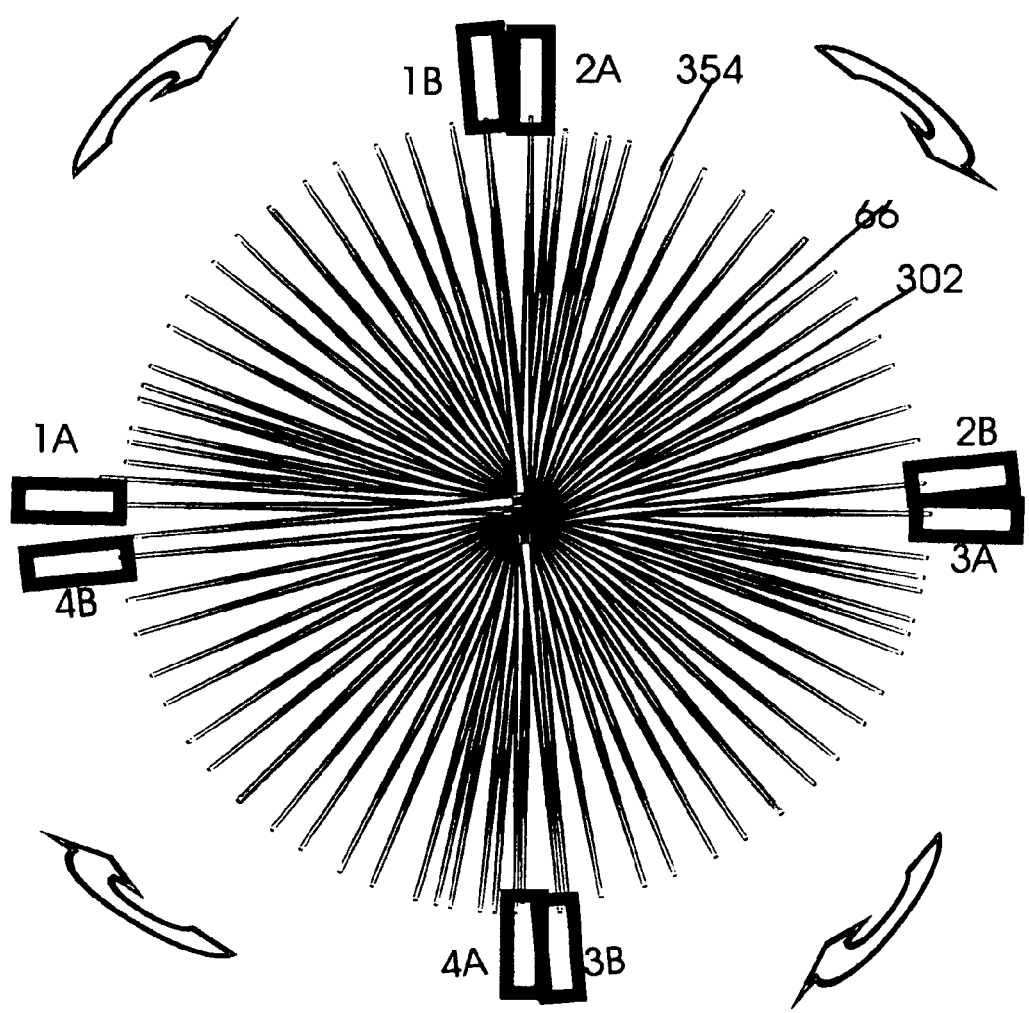

FIG. 3G illustrates four narrow simultaneous beams from all four medical accelerators shown in FIG. 3F as they make a simultaneous 90-degree arc rotation. Each small segment rotational movements of the accelerator contribute one segments of the beam 354 that converges at the isocenter 66. When the first accelerator with its treatment head completes its 90-degree arc rotation, from 270° 1A, to 0° 1B, its beam's energy deposition at the isocentric tumor 302 covers one fourth of the tumor volume. As the accelerator one at 270° starts its clockwise rotation towards the 0° as shown by the arrow, accelerator two at 0° starts its clockwise arc rotation towards 90°, accelerator three at 90° starts its rotation towards 180° and the accelerator four at 180° starts its rotation towards 270°. At completion of the 90° arch rotation, the position of the accelerator one at 270° 1A changes to 1B as the accelerator one reaches at 0°, the position of the accelerator two at 0° 2A changes to 2B as the accelerator two reaches at 90°, the position of the accelerator three at 90° 3A changes to 3B as the accelerator three reaches at 180°, and the position of the accelerator four at 180° 4A changes to 4B as the accelerator two reaches at 270°. Each arc rotation is a 90° rotation. This simultaneous four-arc rotation of all four accelerators renders a well-focused circular high dose region at the isocenter 66. At any given time during this simultaneous arc rotation of all four accelerators, four narrow segment of the target volume is simultaneously exposed to high biological dose rate radiation. The arrows show the direction of the arc rotation of the accelerators.

Figure 3H:
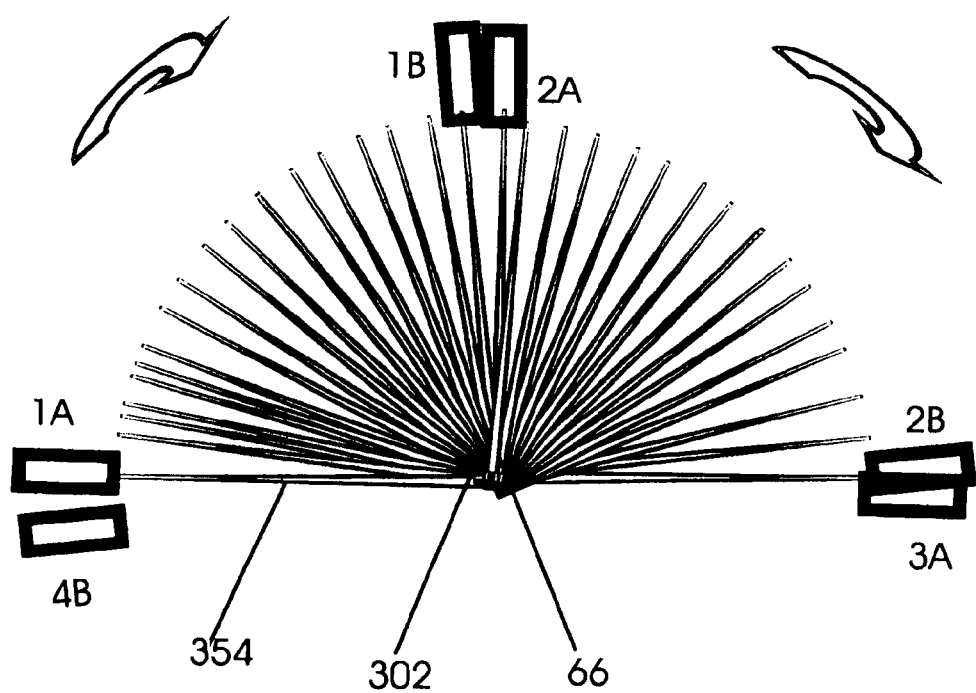

FIG. 3H illustrates two narrow simultaneous beams from only two of the four adjacent accelerators, accelerator 1A at 270° and accelerator 2A at 0° as shown in 3H. They make a simultaneous 90-degree arc rotation. Other two accelerators, 3A and 4A are kept idle. Each small segment rotational movements of one accelerator contribute one single beam 354 segment that converges at the isocenter 66. Simultaneous such two beams from two accelerator treats two small segments of the tumor 302 at the isocenter 66 at a time. Combined, all such simultaneous segments of the beam from the simultaneously rotating two-accelerator make a half circle high dose region in the target tumor 302 at the isocenter 66.

FIG. 3 I illustrate theoretical 201 simultaneous microbeams from 201 radioactive sources all arranged in a circle and all those micro-beams converging at its central isocenter 66. It illustrates the concept of additive dose rate of such converging beams at the isocentric focal point. It is the basis of additive dose rate of brachytherapy and Gamma Knife. The entire 201 single beam 355 converges at the isocenter 66 simultaneously and renders its additive dose rate of about 145 cGy at the isocenter. Each single beam has insignificant dose rate at the isocenter.

Figure 3J:
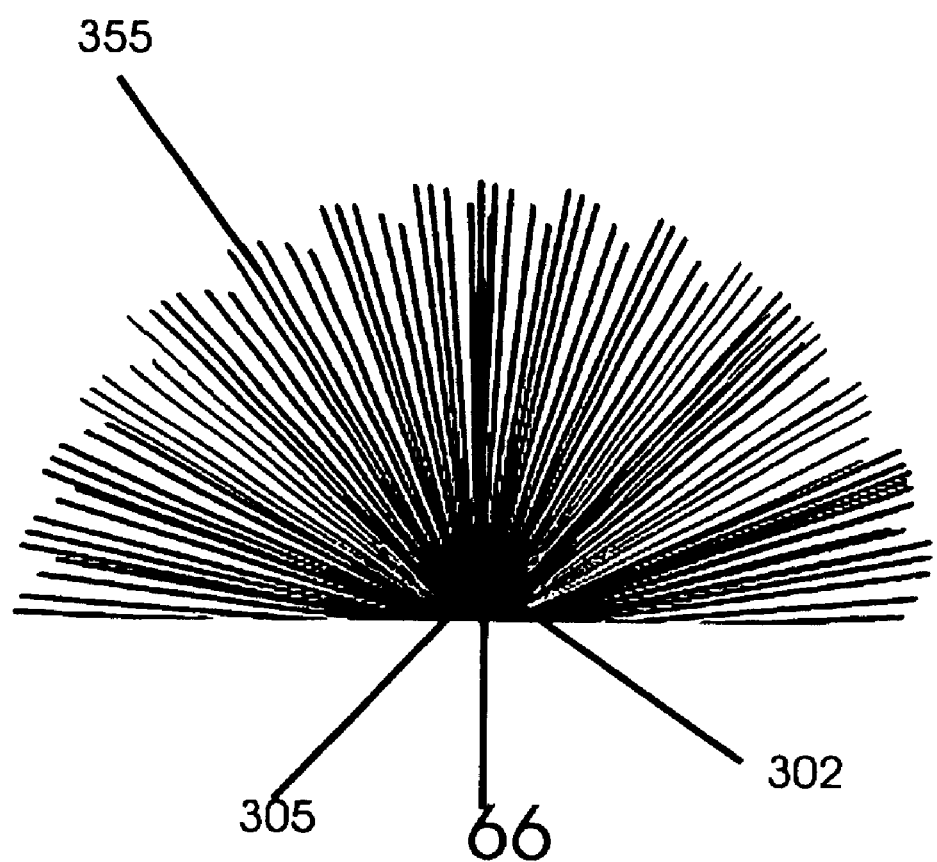

FIG. 3J illustrates theoretical 201 simultaneous microbeams from 201 radioactive sources all arranged in a half-circle hemisphere and all those micro-beams converging at its central focal point. It is also to illustrate the concept of additive dose rate of such converging beams at the isocentric focal point like the additive dose rate of brachytherapy and Gamma Knife. Each single beam 355 converges at the treatment volume tumor 302 at isocenter 66. It renders the isocentric additive biological dose rate 305.

Cobalt-60 has poor LET and dose rate. Its LET is only 0.2 KeV/µ. However, by extrapolating the principles explained before on converging additive LET, multiple simultaneous beams could render additive dose rate and LET. This additive dose rate effect is used to achieve clinically usable dose rate in Gamma Knife radiosurgery. The Gamma Knife has 201 cobalt-60 sources. Each source is of 1 mm in size. The additive LET of 201 simultaneous cobalt 60 beams could be 201×0.2 KeV/µ is 40.2 KeV/µ. In spite of Gamma Knife's very poor dose rate and the Cobalt-60's short half life of 5.26 years, the treatment outcome for trigeminal neuralgia with Gamma Knife is reported as the same when the treatment was rendered during the early and late phase of Cobalt-60's half-life (18). During the later period of cobalt-60's half-life, its dose rate is reduced to half of its original one. The patients treated with Gamma knife during the later part of Cobalt-60's half-life had only about 50-cGy/min-dose rate at the isocenter. Still this low dose rate did not affect the outcome of trigeminal neuralgia (18). From the radiobiological and technical point of views, it is a very poor method radiation therapy and radiosurgery. Still the treatment outcome with machine dose rate of 145 cGy and or 72.5 cGy is reported to be as the same (18). It is associated with Gamma Knife's 201 small Cobalt-60 source's 201 simultaneous beams, all converging into a small target simultaneously and their additive LET of 0.2×201 KeV/μ, 40.2 KeV/μ. However this additive LET effect is over shadowed by the poor dose rate of Gamma knife.

FIG. 3K demonstrates two medical accelerators adapted for simultaneous two-beam radiation therapy and radiosurgery. The accelerators are mounted on to one rotating gantry, one accelerator at each ends of the gantry. The two movable segments of a split magnet that are moved to below the ground to free the treatment room from the magnet. It facilitates the rotation of the gantry with the accelerators without interference from the MRI. The gantry holds two accelerators with treatment heads 2, one at each end. A circular collimator 309 is attached to the treatmenthead 2. It reaches close to the patient when a patient is placed in treatment position on the treatment table (not shown). The mm-sized accelerator source, low beam energy of 2-6 MV and the circular collimator 309 minimizes the penumbra of the beam at the target. The narrow beam from each accelerator is collimated with the circular collimator 309 as it emerges from the accelerator unit. Individual beam's collimation is also carved out from tungsten powder mixture at the time of the single session simulation and treatment. It is described below under methods of operation. Other means of beam collimation that is used includes micro-multileaf collimation. Simultaneously converging single beam 1, 356, and the simultaneously converging single beam 2, 360, from the accelerator treatmentheads 2 converges at the isocenter 66. These two simultaneous beams, that both converging at the isocenter 66 renders its isocentric additive biological dose rate and LET 305. As described before, such simultaneous two-beam radiosurgery has many unique radiobiological advantages. It also helps the conformal treatment of the target tissue with lesser or no radiation to the surrounding normal tissue and critical organs. It is obvious that the positions of the perpendicular gantry as shown in FIG. 3G would change as it rotates around the isocenter 66. The arrows indicate the direction of the rotation. The two movable segments of a split magnet are moved to below the ground. It frees the treatment room from the magnet and enables to rotate the gantry with the accelerator without any interference. As described under FIG. 3D, the open magnet segment 282 and the open magnet segment 284 are retrieved to below the ground 287. The treatment heads, the shielding and other structures are built from non-magnetic material or they are encased in non-magnetic materials.

Figure 3L:
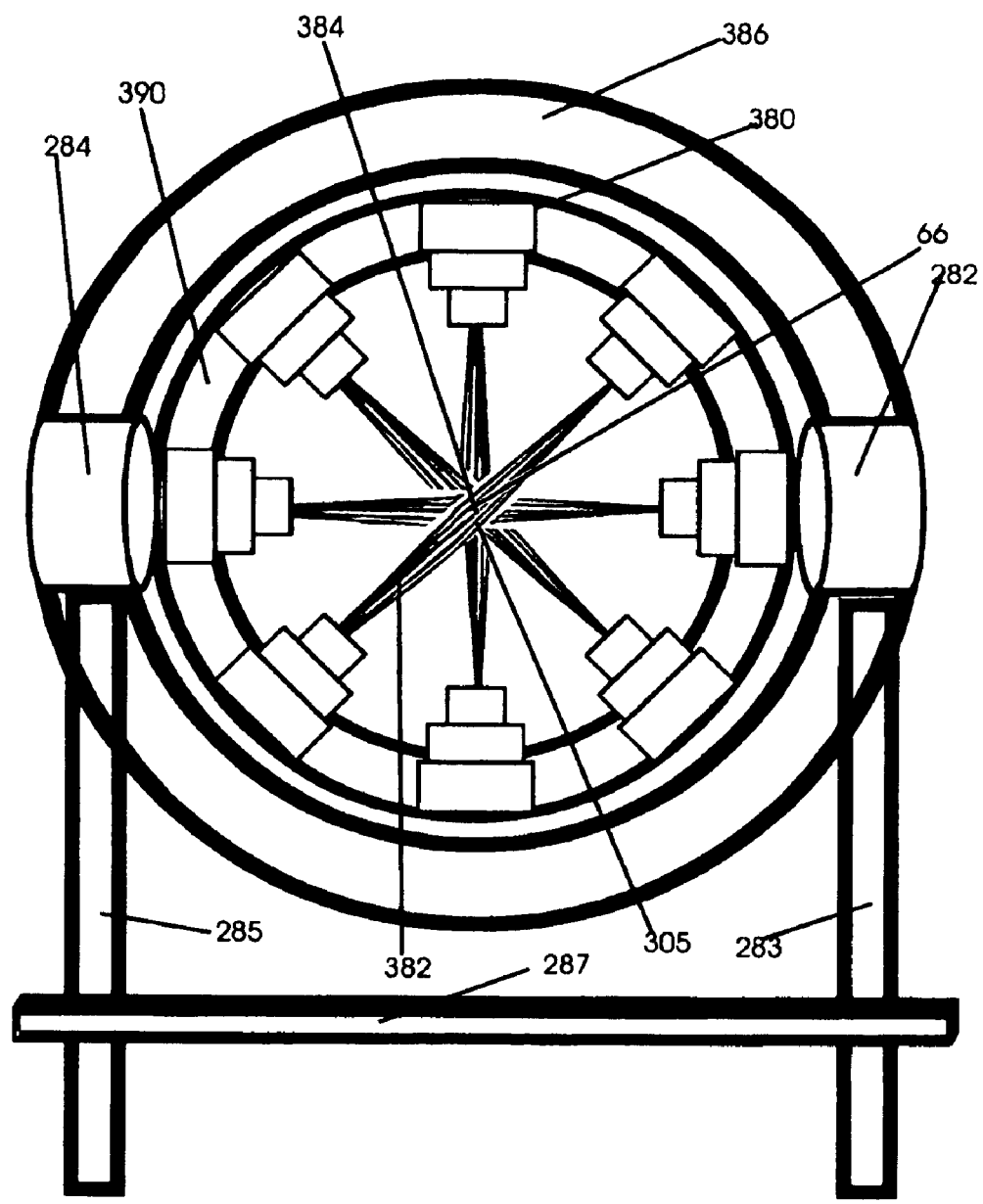
Figure 3M:
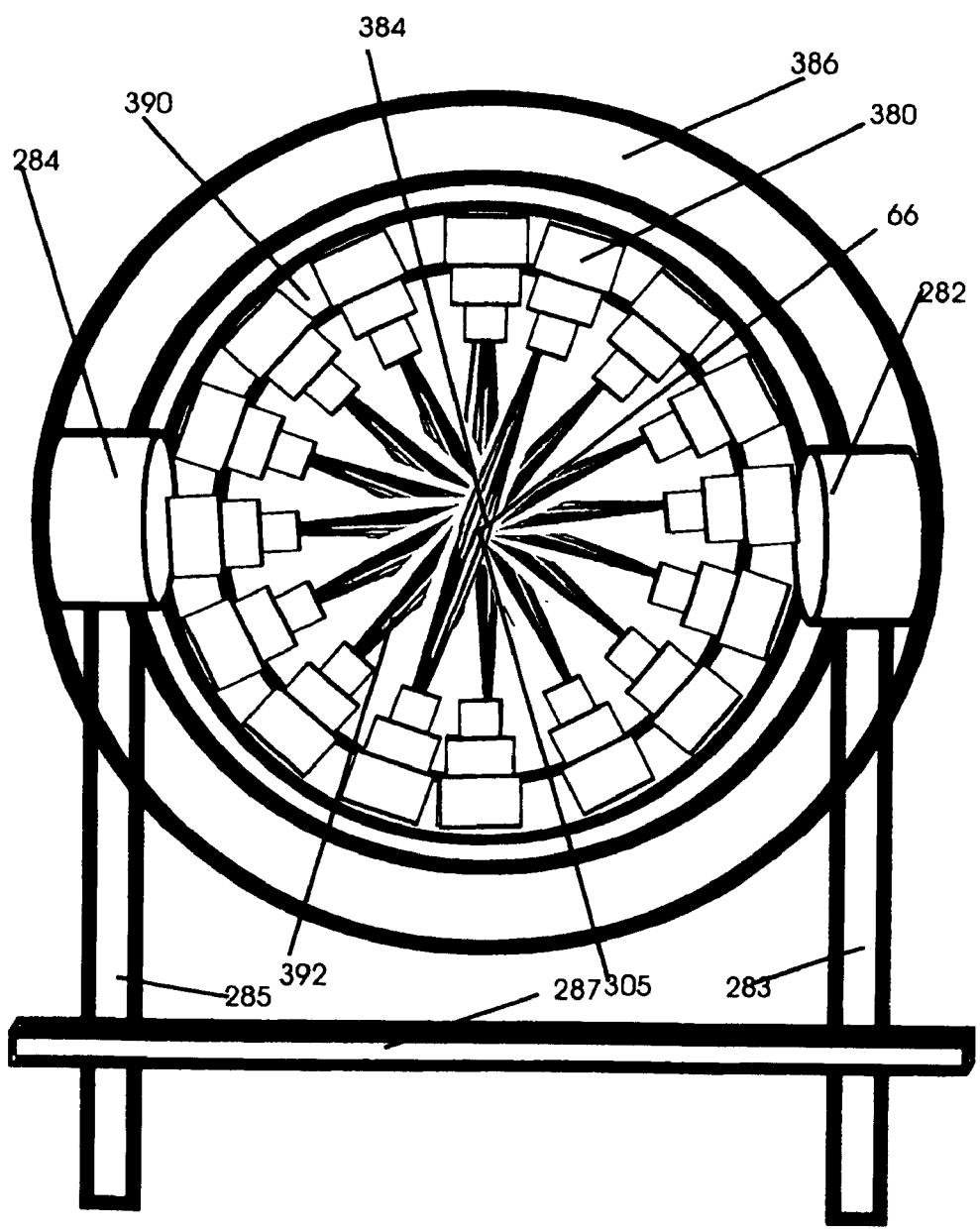
Figure 3N:
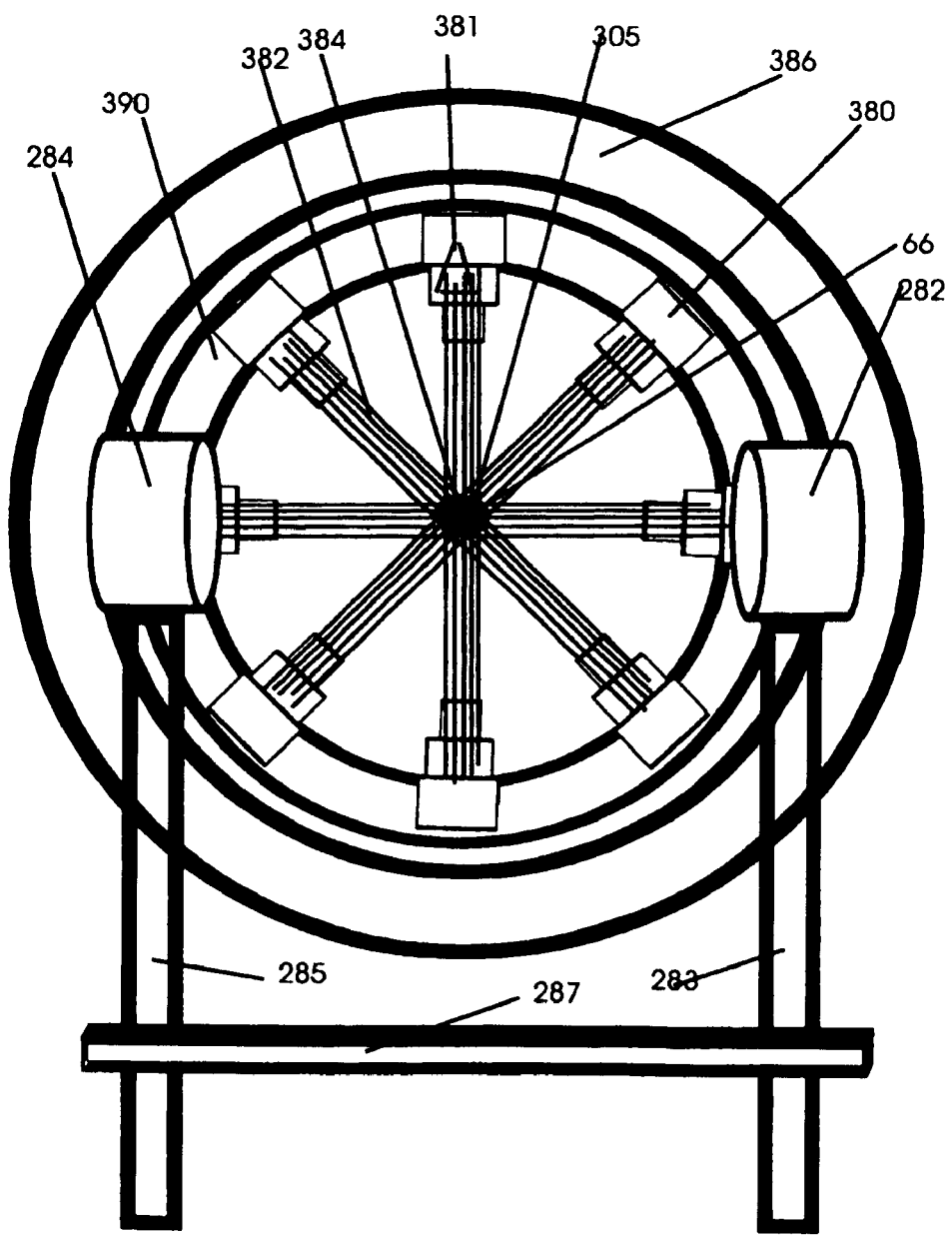

FIGS. 3L-1 demonstrates four pairs of opposing treatment heads each with a single isotopic sources like cobalt-60 and eight such treatment heads arranged in a circle with their simultaneous beams converging at the isocenter for γ-ray teletherapy. The two segments of a split magnet are moved above the ground for MRI guided simultaneous eight beams, γ-ray teletherapy. The treatment heads, the shielding and other structures are built from non-magnetic material or they are encased in non-magnetic materials. Eight treatmentheads 380 containing cobalt-60 sources are mounted on to a radiation shielding circular gantry 386. For rotational treatment, when this gantry is rotated to 45°, the combined eight treatment head's 380 and its eight simultaneous beam's rotational effect is 360°. As described before, after MRI, the open magnet segment one 282 and open magnet segment two 284 are moved back to below the ground. It removes the magnet from the treatment room. The radiation therapy is rendered with simultaneous eight cobalt-60 beams or elective simultaneous two, three, four, five, six, seven, eight cobalt-60 beams either as stationary or as rotational treatment.

The exposure rate constant ($\bullet$., $Rm^2 h^{-1} Ci^{-1}$) for one Ci Co-60 at 1 meter per hour is 1.29, (25). When the distance is reduced from 1 meter to 0.8 meter (from 100 cm to 80 cm, this exposure rate constant, $\bullet$. becomes $1.29\times(100/80)^2$ or 2.0156 R/h. Hence the exposure rate for 1 Ci $^{60}$C at 80 cm is 2.0156 R/h. Then the exposure rate for 5,000 Ci $^{60}$C source at 80 cm distance is 10,078 R per hour or 168 R/min. Taking the Roentgen to rads conversion factor as 0.876, the dose rate for 5,000 Ci $^{60}$C at 80 cm distance from the source is 168/0.876 is 192 cGy/min. With eight simultaneous 5,000 Ci $^{60}$C sources beam has 192×8 cGy/min or 1,536 cGy dose rates at 80-cm distance. If the source strength in each treatment head is reduced to 1,000 Ci instead of 5,000 Ci, then the dose rate at 80 cm for such eight Ci $^{60}$C sources at 80-cm distance is 307 cGy/min. This multiple simultaneous $^{60}$Co beam method of treatment reduces the single $^{60}$Co beam's low dose rate associated radiobiological deficiencies but to the extent to the much higher dose rate Linac. The present method of treating a tumor with a single $^{60}$Co beam suffers low dose rate and hence it's poor radiobiological effectiveness.

When the source distance is reduced from 1 meter to 0.6 meter, the exposure rate constant $\bullet$. for 1 Ci $^{60}$C becomes $1.29\times(100/60)^2$ or 3.5833 R/h. In this instance, the exposure rate for 5,000 Ci $^{60}$C source at 60-cm distance is 3.6833×5,000 or 17,917 R per hour or 298.6 R per min. Taking the Roentgen to rads conversion factor as 0.876, the dose rate for 5,000 Ci $^{60}$C at 60-cm distance is 298.6 R/0.876 is 341 cGy/min. With eight 5,000 Ci $^{60}$C source simultaneous beams all converging at the focal point 60-cm distance from the source is 341×8 or 2,728 cGy/min. If the source strength in each treatment head were reduced to 1,000 Ci instead of 5,000 Ci, then the combined dose rate at 60 cm for such eight Ci $^{60}$C source beams would be 545 cGy/min.

If it were eight fields, single session, 800-cGy-radiation therapy or radiosurgery, with eight $^{60}$C-beams, the dose delivered by each beam to each field to the tumor at the isocenter 66 is 100 cGy. Because of the much improved radiobiological effectiveness of the multiple simultaneous beam method of treatment, a lower dose than the conventional radiosurgical dose is necessary to achieve the same or superior tumor cure and control. A beam with the dose rate of 341 cGy/min when the distance from the source is 60 and with the following treatment parameters, average tissue maximum ratio (TMR) 0.746, collimator scatter factor ($S_c$) 0.98, phantom scatter factor ($S_p$) 0.99, and the isocenter distance from the source 100 cm, then $D_{iso}$ is 341×0.98×0.99×0.746 is 247 cGy at the isocenter (26). For a simple calculation aimed to show the advantages of treating a tumor with multiple simultaneous beams, the parameters for calculation of the dose rate at the isocenter, $D_{iso}$, is kept as the same as in the reference quoted. In fact the referenced calculation is for a 4 MV beam. There is minor difference in the average TMR for $^{60}$Co and 4 MV beams at depth but it is ignored. The treatment time to deliver 100 cGy at $D_{iso}$, the isocenter is $100/247$ is 0.4049 min or 24.29 seconds. Alternatively, eight such beam's additive biological dose rate at the isocenter is 1,976 cGy. Hence the time to deliver 800 cGy to the isocenter by all the beams combined is $800/1,976$ min or 0.4049 min or 24.29 seconds. Since all the eight fields are treated with eight simultaneous beams and 100-cGy/beam tumor dose, its additive dose to the tumor at the isocenter 66 is 800 cGy. A patient with no acute respiratory symptoms can hold breathing during this 24.29 seconds beam on time easily. Along with other major radiobiological advantages of simultaneous treatment of all the fields that were described before, this short duration beam on time also enables breathing synchronized precision radiation therapy.

FIG. 3L 2 demonstrates eight parallel opposing, four pairs of opposing treatment heads each with five isotopic sources like cobalt-60 and eight such treatment heads arranged in a circle with their simultaneous beams converging at the isocenter for short duration, high dose rate γ-ray teletherapy and radiosurgery but with less than 15 or 30 cGy $^{60}$Co $d_{max}$ dose.

By inserting a microbeam collimator of the kind referred in the patent of Slatkin et al (6) in the path of these converging beams, converging microbeam is obtained. Alternatively, by inserting small wires into the block made of pliable tungsten powder mixture made for each patent and removing them from the block, micro-channels for microbeam are created within the block. With multiple simultaneous such microbeams from a number of treatmentheads in a circle at varying angles as shown in this figure, much superior, with additive dose rate simultaneous microbeams at the isocenter is obtained. Its dose to the normal tissue is much lesser than those reported by Slatkin et al. Hence it is a much superior microbeam system than those described by Slatkin et al (6).

The two segments of a split magnet are moved above the ground for MRI guided simultaneous eight beams, γ-ray teletherapy. Similar MRI guided radiation therapy is illustrated and described here, under FIG. 1, FIG. 2, FIG. 3 C, FIG. 3 D, FIG. 3 E, FIG. 3 F, FIG. 3 K, FIGS. 3L-1, FIGS. 3L-2, FIG. 3M, FIG. 3N 1, FIG. 3 N2 and FIG. 3 N3. The treatment heads, the shielding and other structures are built from non-magnetic material or they are encased in non-magnetic materials.

Eight treatment-heads 380 containing cobalt-60 sources are mounted on to a radiation shielding circular gantry 386. For rotational treatment, when this gantry is rotated to 45°, the combined eight treatment head's 380 and its eight simultaneous beam's rotational effect is 360°. As described before, after MRI, the open magnet segment one 282 and open magnet segment two 284 are moved back to below the ground to remove the magnet from the treatment room. The radiation therapy is rendered with simultaneous eight cobalt-60 beams or elective simultaneous two, three, four, five, six or seven cobalt-60 beams either as stationary or as rotational treatment.

The exposure rate constant (•., Rm$^2$ h$^{-1}$ Ci$^{-1}$) for one Ci Co-60 at 1 meter per hour is 1.29, (25). When the distance is reduced from 1 meter to 0.8 meter (from 100 cm to 80 cm, this exposure rate constant, •. becomes 1.29×(100/80)$^2$ or 2.0156 R/h. Hence the exposure rate for 1 Ci $^{60}$C at 80 cm is 2.0156 R/h. Then the exposure rate for each of the 1,000 Ci $^{60}$C source at 80 cm distance is 2.015×1000 R per hour or 34 R per min. Taking the Roentgen to rads conversion factor as 0.876, the dose rate for 1,000 Ci $^{60}$C at 80 cm distance from the source is $^{34}/_{0.876}$ is 38.348 cGy/min. Hence the D$_0$ dose for each 1,000 Ci $^{60}$Co beam is 38 cGy/min.

A beam with the D$_0$ dose rate of 38 cGy/min and with the following treatment parameters, average tissue maximum ratio (TMR) 0.746, collimator scatter factor (S$_c$) 0.98, phantom scatter factor (S$_p$) 0.99, (26, p 217) has the D$_{iso}$ dose rate of 38×0.98×0.99×0.746 cGy/min, that is 27.5 or say 28 cGy/min. For a simple calculation aimed to show the advantages of treating a tumor with multiple simultaneous beams, the parameters for calculation of the dose rate at the isocenter, D$_{iso}$ is kept as the same as in the reference quoted. In fact the referenced calculation is for a 4 MV beam. There is minor difference in the average TMR for $^{60}$Co and 4 MV beams at depth but it is ignored. Since the beams arriving at isocenter 66 from each of eight treatment heads 381 and since the treatment heads are arranged at 45° angels in a circle, the average TMR at the isocenter could be taken for dose calculations. It is like taking the average TMR for dose calculations for rotational treatment. Hence for 1,000 Ci $^{60}$Co at 80-cm distance from the source the D$_0$ dose rate is 38 cGy/min and the D$_{iso}$ dose rate at isocenter 66 is 28 cGy/min. There are five 1,000 Ci $^{60}$Co sources in each treatment heads and all the five beams from these sources converge at the isocenter simultaneously. Their combined dose rate at isocenter is 140 cGy. There are forty simultaneous beams from eight treatment heads, all converging at the isocenter. Hence the combined dose rate at the isocenter for all these forty simultaneous beams is 28×40 which is 1,120 cGy. It renders high additive biological dose rate and LET 305 at the isocenter 66.

When the distance is reduced from 1 meter to 0.6 meter, the exposure rate constant (•., Rm$^2$ h$^{-1}$ Ci$^{-1}$) for one Ci Co-60 is 1.29×(100/60)$^2$ or 3.5833 R/h. Hence the exposure rate for 1 Ci $^{60}$Co at 60 cm is 3.5833 R/h and the exposure rate for 1,000 Ci $^{60}$Co source at 60 cm distance is 3.5833×1,000 which is 3,583.33 R per hour or 59.722 R per min. Taking the Roentgen to rad conversion factor as 0.876, the dose rate for 1,000 Ci $^{60}$Co at 60 cm distance from the source is $^{59.722}/_{0.876}$ which is 68.646 cGy/min or 69 cGy/min. It is the D$_0$ and D$_{max}$ dose rate for each 1000 Ci $^{60}$Co sources at 60-cm distance from the source. As shown above, the dose rate at isocenter, D$_{iso}$=D$_0$× S$_c$×S$_p$×Average TMR (26, p 217). Therefore its D$_{iso}$ dose rate is 69×0.98×0.99×0.746 cGy/min, that is 49.94 or 50 cGy/min. There are forty beams converging at the isocenter 66. In this instance, their combined dose rate D$_{iso}$ is 50×40, which is 2,000 cGy. It renders high additive biological dose rate and LET 305 at the isocenter 66.

If it were eight fields, single session, 800-cGy-radiation therapy or radiosurgery, with 40 $^{60}$C-beams, the dose delivered by each beam at the isocenter 66 is 20 cGy. Because of the much improved radiobiological effectiveness of the multiple simultaneous beam method of treatment, a lower dose than the conventional radiosurgical dose is necessary to achieve the same or superior tumor cure and control. When the distance from the source is 80 cm, the D$_{iso}$ dose is 28 cGy/min.

Hence the treatment time to deliver 20 cGy at the isocenter is $^{20}/_{28}$ min, which is 0.7143 min or 42.85 seconds. It is relatively a longer period for a patient to hold the breathing while the beam is on. When the distance from the source is 60 cm, the D$_{iso}$ dose is 50 cGy/min. Hence the treatment time to deliver 20 cGy at the isocenter is $^{20}/_{50}$ min, which is 0.4 min or 24 seconds. A patient with no acute respiratory symptoms can hold breathing during the above 24 second beam on time. It enables breathing synchronized precision radiation therapy easier.

Previously, the D$_0$ dose rate for this machine's each 100 Ci $^{60}$Co source was calculated as 69 cGy/min when the distance from the $^{60}$Co source is 60 cm. Hence the total monitor units to be set to deliver 20 cGy at the isocenter is are 69×0.4 is 27.6. Hence the maximum dose to normal tissue is 28 cGy plus the exit dose from the opposing beam. The exit dose contribution is about 45 percent of the entrance dose at the opposite side. In this instance, the maximum dose to the normal tissue is monitor unit setup dose of 28 cGy plus about 45 percent of this D$_{max}$ dose, which is 28 plus 13 cGy, which is 41 cGy. Hence its total dose to normal tissue at D$_{max}$ is 28 plus 13 that is 41 cGy. Therefore, this multiple simultaneous $^{60}$Co beam method of treatment eliminates the single much higher source strength $^{60}$Co beam's high dose to normal tissue, at D$_{max}$ below the skin that cause severe normal tissue damage. It is further explained below.

A conventional 5,000 Ci strength $^{60}$Co beam at 60-cm distance from the source has D$_0$ dose rate of 341 cGy/min. It is derived as the following. The exposure rate constant (•., Rm$^2$ h$^{-1}$ Ci$^{-1}$) for one Ci Co-60 at 1 meter per hour is 1.29, (25), the distance is reduced from 1 meter to 0.6 meter. Then the exposure rate constant, •, becomes $1.29 \times (100/60)^2$ or 3.5833 R/h. Hence the exposure rate for 5,000 Ci $^{60}$Co source at 60 cm distance is $3.5833 \times 5,000$ which is 17,916.66 R per hour or 298.61 R per min. Taking the Roentgen to rads conversion factor as 0.876, the dose rate for 5,000 Ci $^{60}$Co at 60 cm distance from the source is $^{298.61}/_{0.876}$ which is 340.8 or 341 cGy. It is the $D_0$ and $D_{max}$ dose rate for each 5000 Ci $^{60}$Co sources at 60-cm distance from the source.

If a tumor at isocenter were treated by the conventional four-field technique with single treatment head and a single $^{60}$Co source and the tumor dose were 800 cGy, then the isocentric dose from each beam is 200 cGy. The time to deliver 200 cGy at isocenter then will be 200/$D_{iso}$ 247 is 0.8097 min or 48.58 seconds. Its MU set up is $341 \times 0.8097$ is or 276 MU. Therefore, its maximum dose to the normal tissue at $D_{max}$ that is below the skin is 276 cGy plus about 45 percent of the $D_{max}$ from the opposing beam, which is 122 cGy. Hence the total dose to normal tissue at $D_{max}$ is 276 plus 122 that is 398 cGy. Thus when a tumor is treated by four-field setup and the single session tumor dose is 800 cGy, then the combined $D_{max}$ dose and the exit dose at $D_{max}$ is 398 cGy. It is an unacceptable high dose to normal tissue. On the contrary, treating a tumor to a single dose of 800 cGy with simultaneous 4.0 beams by the method of $D_0$ source distance 60 cm and $D_{iso}$ dose of 50 cGy as described in this invention reduces the maximum dose to normal tissue from 398 to 41 cGy.

FIG. 3 M demonstrates sixteen parallel opposing, eight pairs of opposing isotopic sources like sixteen cobalt-60 sources arranged in a circle for simultaneous sixteen-beam, γ-ray teletherapy. The two movable segments of a split magnet are moved above the ground for MRI guided simultaneous eight beams, γ-ray teletherapy. Similar MRI guided radiation therapy is illustrated and described here, under FIG. 1, FIG. 2, FIG. 3 C, FIG. 3 D, FIG. 3 E, FIG. 3 F, FIG. 3 K, FIGS. 3L-1, FIGS. 3L-2, FIG. 3M, FIG. 3N 1, FIG. 3 N2 and FIG. 3 N3. The treatment heads, the shielding and other structures are built from non-magnetic material or they are encased in non-magnetic materials.

Sixteen treatment-heads 380 containing cobalt-60 sources are mounted on to a radiation shielding circular gantry 386. For rotational treatment, when this gantry is rotated to 22.5°, the combined sixteen treatment head's 380 and its sixteen simultaneous beam's rotational effect is 360°. As described before, after MRI, the open magnet segment one 282 and open magnet segment two 284 are moved back to below the ground. It removes the magnet from the treatment room. The radiation therapy is rendered with simultaneous sixteen cobalt-60 beams or elective simultaneous two, three, four, five, six, seven, eight, nine, ten, eleven, twelve, thirteen, fourteen, fifteen or sixteen cobalt-60 beams either as stationary or as rotational treatment.

As described before, the exposure rate for 1 Ci $^{60}$C at 80 cm is 2.0156 R/h. Hence, the exposure rate for 5,000 Ci $^{60}$C source at 80 cm distance is 10,078 R per hour or 168 R per min Taking the Roentgen to rad conversion factor as 0.876, the dose rate for 5,000 Ci $^{60}$C at 80 cm distance from the source is $^{168}/_{0.876}$ is 192 cGy/min. With sixteen simultaneous 5,000 Ci $^{60}$C sources beam has $192 \times 16$ cGy/min or 3,012 cGy dose rates at 80-cm distance. If the source strength in each treatment head is reduced to 1,000 Ci instead of 5,000 Ci, then the dose rate at 80 cm for such five Ci $^{60}$C sources at 80-cm distance is 614 cGy/min.

Also as described before, when the source distance is reduced from 1 meter to 0.6 meter, this exposure rate constant •, for 1 Ci $^{60}$ C. becomes $1.29 \times (100/60)^2$ or 3.5833 R/h. In this instance, the exposure rate for 5,000 Ci $^{60}$C source at 60-cm distance is $3.6833 \times 5,000$ or 17,917 R per hour or 298.6 R per min. Taking the Roentgen to rad conversion factor as 0.876, the dose rate for 5,000 Ci $^{60}$C at 60-cm distance is 298.6 R/0.876 is 341 cGy/min. With sixteen 5,000 Ci $^{60}$C source simultaneous beams all converging at the focal point at 60-cm distance from the source is $341 \times 16$ or 5,546 cGy/min. If the source strength in each treatment head were reduced to 1,000 Ci instead of 5,000 Ci, then the combined dose rate at 60 cm for such sixteen Ci $^{60}$C source beams would be 1,092 cGy/min.

If it were eight fields, single session, 800-cGy-radiation therapy or radiosurgery, with eight $^{60}$C-beams, the dose delivered by each beam to each field to the tumor at the isocenter 66 is 50 cGy. Because of the much improved radiobiological effectiveness of the multiple simultaneous beam method of treatment, a lower dose than the conventional radiosurgical dose is necessary to achieve the same or superior tumor cure and control. A beam with the $D_0$ dose rate of 341 cGy/min, TMR 0.746, $S_c$ 0.98, $S_p$ 0.99, and the isocenter distance from the source 100 cm, then $D_{iso}$ is $341 \times 0.98 \times 0.99 \times 0.746$ is 247 cGy (26). For a simple calculation aimed to show the advantages of treating a tumor with multiple simultaneous beams, the parameters for calculation of the dose rate at the isocenter, $D_{iso}$ is kept as the same as in the reference quoted. In fact the referenced calculation is for a 4 MV beam. There is minor difference in the average TMR for $^{60}$Co and 4 MV beams at depth but it is ignored. The treatment time to deliver 50 cGy at the isocenter, $D_{iso}$, is $^{50}/_{247}$ is 0.2024 min or 12.15 seconds. The monitor unit set up to deliver 50 cGy at the isocenter is $341 \times 0.2024$ is 69 cGy. Alternatively, sixteen such beam's additive biological dose rate at the isocenter is 3,952 cGy. Hence the time to deliver 800 cGy to the isocenter by all the beams combined is $^{800}/_{3,952}$ min or 0.2024 min or 12.15 seconds and the monitor unit setup is 69 cGy. A patient with no acute respiratory symptoms can hold breathing during this beam on time of 12.15 seconds easily. It enables breathing synchronized precision radiation therapy.

When a tumor is treated with a conventional $^{60}$Co machine by conventional parallel opposed four-field technique and the single session tumor dose is 800 cGy, the total dose to normal tissue at $D_{max}$ of each field is the $D_{max}$ dose 276 plus the exit dose of the parallel opposed beam 122, that is 398 cGy. It is an unacceptable high dose to normal tissue. On the contrary, treating a tumor to a single dose of 800 cGy with 16 simultaneous beams as in this FIG III-M, the monitor unit setup for each of the sixteen treatment head to treat each of the sixteen fields is 69 cGy. It is its $D_{max}$ dose. Its parallel opposing beam's exit dose is about 45 percent of it; that is 31 cGy. Hence, the total dose to the normal tissue in this instance is 69 plus 31 cGy that is 100 cGy. This is still very high but it is far less than the 398 cGy maximum dose to normal tissue when a tumor is treated with a 5,000 Ci $^{60}$Co conventional radiation therapy machine by four fields technique and the dose per field is 200 cGy. The forty beam technique described under FIG III-L2 and those that will be described in other embodiments including the eighty beams method in this invention further reduces the above maximum dose to normal tissue from 398 to 41 cGy and to 20 cGy.

FIG. 3 N1 demonstrates eight parallel opposing, four pairs of opposing treatment heads 380 with eight $^{60}$Co sources 381. Eight such treatment heads are arranged in a circle at 45° angle distance. To increase the $^{60}$Co dose rate at the isocenter 66, the source to $D_0$ distance is adjusted to 60 cm. Their simultaneous parallel beams provide an array of cross firing parallel opposed beams at the isocenter. It facilitates breathing synchronized, high-dose rate γ-ray teletherapy and radiosurgery in about 24 seconds beam on time. Each of such $^{60}$Co beam's 382 $d_{max}$ dose is less than 15 cGy.

By inserting a microbeam collimator of the kind referred in the patent of Slatkin et al (6) in the path of these parallel beams, parallel cross firing microbeam is obtained at the isocenter. Alternatively, by inserting small wires into the block made of pliable tungsten powder mixture made for each patent and removing them from the block, micro-channels for microbeam are created within the block. With multiple simultaneous such microbeams from a number of treatmentheads in a circle at varying angles as shown in this figure, much superior, with additive dose rate simultaneous microbeams at the isocenter is obtained. The dose to the normal tissue is much lesser than those reported by Slatkin et al. Hence it is a much superior microbeam system than those described by Slatkin et al (6).

The two segments of a split magnet 282 and 284 are moved to above the ground for MRI guided γ-ray teletherapy. The number $^{60}$Co sources in each treatment head 380 and each source's strength of radioactivity can be increased or decreased to give a desired dose rate at the isocenter without causing much damage to the normal tissue through which each beam passes towards the isocenter and to the opposing treatment head. In this instance, the source strength of $^{60}$Co is elected as 1000 Ci. The above number of five 1000 Ci $^{60}$Co in each treatment head 380 is only an example. Treatment heads 380 are arranged in a circle and their parallel beams pass through the isocenter. It provides an array of cross firing parallel opposed simultaneous beams. The treatment heads 380 mostly absorbs the opposing beam as they exit after passing through the isocenter. The treatment heads thus also serves as beam shields. Since there are eight treatment heads 380 with five $^{60}$Co sources in one treatment head 381, there are 40 simultaneous parallel beams from forty 1,000 Ci $^{60}$Co sources. Radiation therapy is rendered with all of the forty simultaneous micro-parallel cobalt-60 beams. Alternatively, the number of beams selected to suit the treatment of a particular tumor can be varied. If the beams from any treatment heads are not used for the treatment as per a treatment plan then the beams from those treatment heads are completely blocked. As the beams passes through the isocenter 66, they provide a circle of intense $^{60}$Co beam at the isocenter 66.

Each treatment head 380 with the $^{60}$Co sources are fixed to a motor driven circular rotating gantry 390. The treatment heads 380 are arranged at 45° intervals. When each of the eight-treatment heads 380 completes 45° rotation, the combined effect of the rotational beam distribution is 360°. Hence only 45° rotation is needed to complete 360° beam distribution. The $^{60}$Co γ-ray teletherapy and radiosurgery to a patient with this machine is rendered either as static or rotational treatment. If the treatment is rendered as rotational treatment, then it further reduces the dose to normal tissue. However, the combined dose rate at the isocenter that is the biological dose rate of this machine is extremely high. Hence the entire beam on time is only a few seconds. The time taken to rotate the machine would be longer than this short duration beam on time. Therefore, the rotational treatment may not be practical all the time. Still, the gantry 390 can be rotated to a desired angle as part of a treatment setup. The circular rotating gantry 390 is enclosed in a circular radiation shield 386. It minimizes the radiation exposure in the treatment room. It also renders the construction of the treatment room for such a $^{60}$Co-machine with lesser radiation shielding wall thickness.

The two segments of a split magnet 282 and 284 are moved above the ground for MRI guided γ-ray teletherapy. Similar MRI guided radiation therapy is illustrated and described under FIG. 1, FIG. 2, FIG. 3 C, FIG. 3 D, FIG. 3 F, FIG. 3 F, FIG. 3 K, FIGS. 3L-1, FIGS. 3L-2, FIG. 3M, FIG. 3N 1, FIG. 3 N2 and FIG. 3 N3. After MRI, the open magnet segment one 282 and open magnet segment two 284 are moved back to below the ground. It removes the magnet from the treatment room. The treatment heads, the shielding and other structures are built from non-magnetic material or they are encased in non-magnetic materials.

As described before, the exposure rate constant, •. for 1 Ci $^{60}$Co at 60 cm distance from the source is 3.5833 R/h and the exposure rate for 1,000 Ci $^{60}$Co source at 60 cm distance is 3.5833×1,000 which is 3,583.33 R per hour or 59.722 R per min. Taking the Roentgen to rads conversion factor as 0.876, the dose rate for 1,000 Ci $^{60}$Co at 60 cm distance from the source is $^{59.722}/_{0.876}$ which is 68.646 cGy/min or 69 cGy/min. It is the $D_0$ and $D_{max}$ dose rate for each 1000 Ci $^{60}$Co sources at 60-cm distance from the source. Using similar calculation parameters as in reference (22) but ignoring the difference in average TMR for $^{60}$Co and 4 MV, its dose rate at isocenter, $D_{iso}$ is $D_0$ dose 69×TMR 0.746×$S_c$ 0.98×$S_p$ 0.99 is 49.94, say 50 cGy/min.

When each of the five parallel simultaneous beams from the five $^{60}$Co sources in one treatment head 381 reaches at the isocenter 66, they cross fire with similar beams from other seven treatment heads also arriving simultaneously at the isocenter 66. Because of the cross firing effects of these simultaneous beams at the isocenter, the biological dose rate of these five simultaneous beams from one treatment head at the isocenter is 50×5, that is 250 cGy/min. There are eight treatment heads arranged in a circle at 45° angle distance. Hence there are forty 1,000 Ci $^{60}$Co beams cross firing at the isocenter 66. As shown above, each of the 1,000 Ci $^{60}$Co beam's isocentric dose rate is 50 cGy/min. Hence the combined biological dose rate of all the 40 simultaneous beams is 50×4.0 which is 2,000 cGy/min. Thus the simultaneous beams from each of the forty 1,000 Ci sources from eight treatment heads renders high additive biological dose rate and LET 305 at the isocenter 66.

This multiple simultaneous $^{60}$Co beam method of treatment eliminates the single much higher source strength $^{60}$Co beam's high dose to normal tissue at $D_{max}$ below the skin that could cause severe normal tissue damage. It also eliminates the conventional single source $^{60}$Co machine's relatively low dose rate at treatment distance and hence its poor radiobiological effectiveness. The present method of treating a tumor with a single $^{60}$Co beam suffers low dose rate and hence poor radiobiological effectiveness.

If it were eight fields, single session, 800-cGy-radiation therapy or radiosurgery, with 40 $^{60}$C-beams, the dose delivered by each beam at the isocenter 66 is 20 cGy. Because of the much improved radiobiological effectiveness of the multiple simultaneous beam method of treatment, a lower dose than the conventional radiosurgical dose is necessary to achieve the same or superior tumor cure and control. Using the formula $D_{iso}=D_0 \times S_c S_p \times$Average TMR (25, p 217), the $D_{iso}$ for 1,000 Ci $^{60}$Co beam as in this model setup with SSD 60 cm was calculated as 50 cGy/min above. Hence the treatment time to deliver 20 cGy at the isocenter is $^{20}/_{50}$ min, which is 0.4 min or 24 seconds. Previously, the $D_0$ dose rate for each of the machine's 1,000 Ci $^{60}$Co source was calculated as 69 cGy/min. Hence the total monitor units to be set to deliver 20 cGy at the isocenter is are 69×0.4 is 27.6. Hence the maximum dose to normal tissue is 27 cGy plus the exit dose from the opposing beam. Treating a tumor with simultaneous 40 beams as described in this invention reduces the maximum dose to normal tissue than if it were treating a tumor by a conventional machine with a single source. In this instance, the $D_{max}$ dose to the normal tissue is 28 cGy plus about 45 percent of the $D_{max}$ dose from one of the five 1,000 Ci $^{60}$Co parallel opposing beam from the opposing treatment head is 13 cGy. Hence, its total dose to normal tissue at $D_{max}$ is 28 plus 13 that is 41 cGy. This is a major advantage of this system. It delivers very high dose to the tumor at the isocenter while keeping the dose to the normal tissue very low. As described under FIG III-M, its comparative dose to normal tissue when a tumor is treated by four-field parallel opposed method with a conventional 5,000 Ci $^{60}$Co source is 398. Even when a tumor is treated by sixteen fields with sixteen parallels opposed 5,000 Ci $^{60}$Co beams as in FIG III-M, the maximum dose to normal tissue is 100 cGy. In this instance, since all the five beams from each five $^{60}$Co sources in a treatment head are parallel beams and each treatment head is arranged as parallel opposed ones, the combined $D_{max}$ and exit dose at $D_{max}$ of each parallel opposed beam is separate and not the combined five beam's $D_{max}$ and exit dose at $D_{max}$.

A patient with no acute respiratory symptoms can hold breathing during 24-second beam on time as described above. In addition to other major radiobiological advantages of treating a tumor with multiple simultaneous beams described earlier, this system also enables breathing synchronized precision radiation therapy easier.

FIG. 3 N2 demonstrates sixteen parallel opposing, eight pairs of opposing treatment heads 380 with five $^{60}$Co sources 381 in each treatment heads. It differs from FIG. 3 N1 by having sixteen treatment heads instead of eight treatments in FIG. 3 N1. These treatment heads are arranged in a circle at 25.5° angle distance from each other. In this machine configuration, the source to $D_{max}$ distance is changed from 60 cm as in FIGS. 3 N1 to 80 cm. Their simultaneous parallel beams provide an array of cross firing parallel opposed beams at the isocenter 66. It facilitates breathing synchronized, high-dose rate γ-ray teletherapy and radiosurgery in about 12 seconds beam on time. Each of such $^{60}$Co beam's 382 $d_{max}$ dose is 35 cGy/min. The two segments of a split magnet 282 and 284 are moved to above the ground for MRI guided γ-ray teletherapy. The number of $^{60}$Co sources in each treatment head 380 and each source's strength of radioactivity can be increased or decreased to give a desired dose rate at the isocenter. The beams from each treatment head provide an array of five parallel opposed simultaneous beams. They cross fires at the isocenter with beams from other treatment heads 380. The opposing treatment heads 380 mostly absorbs the exiting beam from opposing treatment head as they exit after passing through the isocenter. The treatment heads thus also serves as a beam shields. Since there are sixteen treatment heads 380 with five $^{60}$Co sources in one treatment head 381, there are 80 simultaneous parallel beams from eighty 1,000 Ci $^{60}$Co sources. The radiation therapy is rendered with all of the eighty simultaneous micro-parallel cobalt-60 beams. Alternatively, the number of beams selected to suit the treatment of a particular tumor can be varied. If the beams from any treatment heads are not used for the treatment as per a treatment plan then the beams from those treatment heads are completely blocked. As the beams passes through the isocenter 66, they provide a circle of intense $^{60}$Co beam at the isocenter 66.

Each treatment heads 380 with the $^{60}$Co sources are fixed to a motor driven circular rotating gantry 390. The $^{60}$Co γ-ray teletherapy and radiosurgery to a patient with this machine is rendered either as static or rotational treatment. If the treatment is rendered as rotational treatment, then it further reduces the dose to normal tissue. The gantry 390 can also be rotated to a desired angle as part of a treatment setup. The circular rotating gantry 390 is enclosed in a circular radiation shield 386. It minimizes the radiation exposure in the treatment room. It also renders the construction of the treatment room for such a $^{60}$Co-machine with lesser radiation shielding wall thickness.

By inserting a microbeam collimator of the kind refereed in the patent of Slatkin et al (6) in the path of these parallel beams, parallel cross firing microbeam is obtained at the isocenter. Alternatively, by inserting small wires into the block made of pliable tungsten powder mixture made for each patient and removing them from the block, micro-channels for microbeam are created within the block. With multiple simultaneous such microbeams from a number of treatmentheads in a circle at varying angles as shown in this figure, much superior, with additive dose rate simultaneous microbeams at the isocenter is obtained. Its dose to the normal tissue is much lesser than those reported by Slatkin et al. Hence it is a much superior microbeam system than those described by Slatkin et al (6).

The two segments of a split magnet 282 and 284 are moved above the ground for MRI guided γ-ray teletherapy. Similar MRI guided radiation therapy is illustrated and described under FIG. 1, FIG. 2, FIG. 3 C, FIG. 3 D, FIG. 3 E, FIG. 3 F, FIG. 3 K, FIGS. 3L-1, FIGS. 3L-2, FIG. 3M, FIG. 3N 1, FIG. 3 N2 and FIG. 3 N3. After MRI, the open magnet segment one 282 and open magnet segment two 284 are moved back to below the ground. It removes the magnet from the treatment room. The treatment heads, the shielding and other structures are built from non-magnetic material or they are encased in non-magnetic materials.

As described before, the exposure rate constant, •. for 1 Ci $^{60}$Co at 60 cm distance from the source is 3.5833 R/h and the exposure rate for 1,000 Ci $^{60}$Co source at 60 cm distance is 3.5833×1,000 which is 3,583.33 R per hour or 59.722 R per min. Taking the Roentgen to rad conversion factor as 0.876, the dose rate for 1,000 Ci $^{60}$Co at 60 cm distance from the source is $^{59.722}/_{0.876}$ which is 68.646 cGy/min or 69 cGy/min. Using similar calculation parameters as in reference 21 (21) but ignoring the difference in average TMR for $^{60}$Co and 4 MV, its dose rate at isocenter, $D_{iso}$ is $D_0$ dose 69×TMR 0.746× $S_c$ 0.98×$S_p$ 0.99 is 49.94, say 50 cGy/min.

Like in FIG. 3 N1, when each of the five parallel simultaneous beams from the five $^{60}$Co sources in one treatment head 381 reaches at the isocenter 66, they cross fire with similar beams from other seven treatment heads also arriving simultaneously at the isocenter 66. Because of the cross firing effects of these simultaneous beams at the isocenter, the biological dose rate of these five simultaneous beams from one treatment head at the isocenter is 50×5, that is 250 cGy/min. There are sixteen treatment heads arranged in a circle at 45° angle distance. Hence there are eighty 1,000 Ci $^{60}$Co beams cross firing at the isocenter 66. As shown above, each of the 1,000 Ci $^{60}$Co beam's isocentric dose rate is 50 cGy/min. Hence the combined biological dose rate of all the 80 simultaneous beams is 50×80 which is 4,000 cGy/min. Thus the simultaneous beams from each of the eighty 1,000 Ci sources from eight treatment heads renders high additive biological dose rate and LET 305 at the isocenter 66.

This multiple simultaneous $^{60}$Co beam method of treatment eliminates the single much higher source strength $^{60}$Co beam's high dose to normal tissue at $D_{max}$ below the skin that could cause severe normal tissue damage. It also eliminates the conventional single source $^{60}$Co machine's relatively low dose rate at treatment distance and hence its poor radiobiological effectiveness. The present method of treating a tumor with a single $^{60}$Co beam suffers low dose rate and hence poor radiobiological effectiveness.

If it were eight fields, single session, 800-cGy-radiation therapy or radiosurgery, with eighty $^{60}$C-beams, the dose delivered by each beam at the isocenter 66 is 10 cGy. Because of the much improved radiobiological effectiveness of the multiple simultaneous beam method of treatment, a lower dose than the conventional radiosurgical dose is necessary to achieve the same or superior tumor cure and control. Using similar calculation parameters as in reference 21 (26) but ignoring the difference in average TMR for $^{60}$Co and 4 MV, its dose rate at isocenter, $D_{iso}$ is $D_0$ dose 69×TMR 0.746×$S_c$ 0.98×$S_p$ 0.99 is 49.94, say 50 cGy/min. Hence the treatment time to deliver 10 cGy at the isocenter is $^{10}/_{50}$ min, which is 0.2 min or 12 seconds. Previously, the $D_0$ dose rate for this machine's each 1000 Ci $^{60}$Co source was calculated as 69 cGy/min. Hence the total monitor units to be set to deliver 10 cGy at the isocenter is 69×0.2 is 13.8. Hence the maximum dose to normal tissue is 14 cGy plus the exit dose from the opposing beam. Treating a tumor with simultaneous 80 beams as described in this invention reduces the maximum dose to normal tissue than if it were treating a tumor by a conventional machine with a single source. In this instance, the $D_{max}$ dose to the normal tissue is 14 cGy plus about 45 percent of the $D_{max}$ dose from one of the five 1,000 Ci $^{60}$Co parallel opposing beam from the opposing treatment head is 6 cGy. Hence its total dose to normal tissue at $D_{max}$ is 14 plus 6, that is 20 cGy. This is a major advantage of this system. It delivers very high dose to the tumor at the isocenter while keeping the dose to the normal tissue very low. As described under FIG III-M, its comparative dose to normal tissue when a tumor is treated by four-field parallel-opposed method with a conventional 5,000 Ci $^{60}$Co source is 398. Even when a tumor is treated by sixteen fields with sixteen parallels opposed 5,000 Ci $^{60}$Co beams as in FIG III-M, the maximum dose to normal tissue is 100 cGy. In this instance, since all the five beams from each five $^{60}$Co sources in a treatment head are parallel beams and each treatment head is arranged as parallel opposed ones, the combined $D_{max}$ and exit dose at $D_{max}$ of each parallel opposed beam is separate and not the combined five beam's $D_{max}$ and exit dose at $D_{max}$.

A patient with no acute respiratory symptoms can hold breathing during 12-second beam on time as described above. In addition to other major radiobiological advantages of treating a tumor with multiple simultaneous beams described earlier, this system also enables breathing synchronized precision radiation therapy easier.

By increasing the distance from 60 cm to 80, the exposure rate constant for one Ci $^{60}$Co- at 80 cm becomes 2.0156 R/h. Hence the exposure rate for 1,000 Ci $^{60}$Co source at 80 cm distance is 2.0156×1,000 which is 2,016 R per hour or 34 R per min. Taking the Roentgen to rad conversion factor as 0.876, the dose rate for 1,000 Ci $^{60}$Co at 80 cm distance from the source is $^{34}/_{0.876}$ which is 39 cGy/min. It is the $D_0$ and $D_{max}$ dose rate for each 1000 Ci $^{60}$Co sources at 80-cm distance from the source. The dose rate at isocenter, $D_{iso}=D_0\times TMR\times S_c\times S_p$ (25, p 217). The $D_0$ dose rate for 1000 Ci $^{60}$Co source at 80-cm distance is 39 cGy/min. The $D_{iso}$, the dose at isocenter is $D_0$ 39×TMR 0.746×S, 0.98×$S_p$ that is 28 cGy/min. Hence when the distance from 1,000 Ci $^{60}$Co source is 80 cm, the dose rate at isocenter 66 is 28 cGy/min.

When each of the five parallel simultaneous beams from the five $^{60}$Co sources in one treatment head 381 reaches at the isocenter 66, they cross fire with similar beams from other fifteen treatment heads also arriving simultaneously at the isocenter 66. Because of the cross firing effects of these simultaneous beams at the isocenter, the biological dose rate of these five simultaneous beams from one treatment head at the isocenter is 28×5, that is 140 cGy/min. There are sixteen treatment heads arranged in a circle at 25.5° angle distance. Hence there are eighty 1,000 Ci $^{60}$Co beams cross firing at the isocenter 66. Hence the combined biological dose rate of all the 80 simultaneous beams is 28×80 which is 2,240 cGy/min.

The dose rate for 1,000 Ci $^{60}$Co at isocenter when the distance from the source is 80 cm is shown to be 39 cGy/min. The isocentric dose, $D_{iso}$ is shown to be 28 cGy/min. Hence the treatment time to deliver 10 cGy at the isocenter is $^{10}/_{28}$ min, which is 0.3571 min or 21.43 seconds. Hence the total monitor units to be set to deliver 10 cGy at the isocenter are 39×0.3571 is 14. The maximum dose to normal tissue is the $D_{max}$ dose 14 cGy plus the exit dose at $D_{max}$ 6 cGy, hence 20 cGy. A patient with no acute respiratory symptoms can hold breathing during the above 21.43 second beam on time. It enables breathing synchronized precision radiation therapy easier.

FIG. 3 N3 demonstrates eight parallel opposing treatment heads, four pairs with four isotopic sources like cobalt-60 in each treatment head and four with single Linac x-ray beam. By virtue of the physical characteristics, the $^{60}$Co beam at the isocenter is a divergent beam. The Linac x-ray beam is used either as a divergent beam when the flattening filter is inserted or as a pencil beam without the flattening filter. The pencil beam has more penetrating power. A 6 MV pencil beam's penetrating power is like that of a 17 MV beam with the flattening filter. This $^{60}$Co and Linac x-ray beam combination facilitates intensity modulated radiation therapy to a tumor with varying depth much easier. The $^{60}$Co is used to treat the lesser depth portion of the tumor and the Linac x-ray beam is used to treat the deeper portion of the tumor. In this instance, the conventional intensity modulation with multileaf collimator, wedges or by other such known means is not needed.

Eight such treatment heads are arranged in a circle with their simultaneous parallel beams providing an array of cross firing simultaneous beams at the isocenter for combined γ-ray and Linac x-ray beam for radiosurgery and radiation therapy. The two segments of a split magnet are also shown as moved to above the ground for MRI guided simultaneous eight beams, combined Linac x-ray and γ-ray radiation therapy. The treatment heads, the shielding and other structures are built from non-magnetic material or they are encased in non-magnetic materials.

It demonstrates four pairs of opposing treatment heads 380. Each of the four treatment heads are equipped with five $^{60}$Co sources 381. The other four treatment-heads are equipped for single Linac-x-ray beam 396. The treatment heads are arranged in a circle at 45° angle distance from each other. The source to $D_0$ distance in this instance is 80 cm. The $^{60}$Co simultaneous parallel beams provide an array of cross firing parallel opposed beams at the isocenter 66. Four-treatment head 398 is equipped to produce Linac x-ray beams. They also converge at the isocenter 66.

By inserting a microbeam collimator of the kind referred in the patient of Slatkin et al (6) in the path of both the $^{60}$Co source's parallel beams and the Linac's x-ray parallel pencil beam, parallel cross firing microbeam is obtained at the isocenter. Alternatively, by inserting small wires into the block made of pliable tungsten powder mixture made for each patient and removing them from the block, micro-channels for microbeam are created within the block. With multiple simultaneous such microbeams from a number of treatment-heads in a circle at varying angles as shown in this figure, much superior microbeams are generated. It is a much superior microbeam combination of 60Co and Linac-x-ray beams. Its dose rate at the isocenter is the additive dose rate of all the beams. Its dose to the normal tissue is much lesser than those reported by Slatkin et al. Hence it is a much superior microbeam system than those described by Slatkin et al (6).

The two segments of a split magnet 282 and 284 are moved to above the ground for MRI guided combined Linac x-ray beam and γ-ray radiation therapy. The opposing treatment heads 380 mostly absorbs the exiting beam from opposing treatment head as they exit after passing through the isocenter. The treatment heads thus also serves as a beam shields. Since there are four treatment heads 380 with five $^{60}$Co sources 381 in each one of them, there are 20 simultaneous parallel beams from twenty 1,000 Ci $^{60}$Co sources. The radiation therapy is rendered with all of the 20 simultaneous microparallel cobalt-60 beams 382 combined with 4 Linac x-ray beam 396. Alternatively, the number of beams selected to suit the treatment of a particular tumor can be varied. If the beams from any treatment heads are not used for the treatment as per a treatment plan then the beams from those treatment heads are completely blocked. As the beams passes through the isocenter 66, they provide an intense focus combined Linac x-ray beam and $^{60}$Co beam at the isocenter 66.

The treatment heads 380 of the $^{60}$Co sources and the Linac treatment heads 398 are fixed to a motor driven circular-rotating gantry 390. The radiation therapy and radiosurgery to a patient with this machine is rendered either as static or rotational treatment. If the treatment is rendered as rotational treatment, then it further reduces the dose to normal tissue. The gantry 390 can also be rotated to a desired angle as part of a treatment setup. The circular rotating gantry 390 is enclosed in a circular radiation shield 386. It minimizes the radiation exposure in the treatment room. It also renders the construction of the treatment room for such a $^{60}$Co-machine with lesser radiation shielding wall thickness. The two segments of a split magnet 282 and 284 are moved above the ground for MRI guided combined Linac x-ray and γ-ray teletherapy. After MRI, the open magnet segment one 282 and open magnet segment two 284 are moved back to below the ground. It removes the magnet from the treatment room.

As described before, the exposure rate constant at 80-cm distance from the source, for 1 Ci $^{60}$Co is 2.0156 R/h. Hence the exposure rate for 1,000 Ci $^{60}$Co source at 80 cm distance is 2.0156×1,000 which is 2,016 R per hour or 34 R per min. Taking the Roentgen to rad conversion factor as 0.876, the dose rate for 1,000 Ci $^{60}$Co at 80 cm distance from the source is $^{34}/_{0.876}$ which is 39 cGy/min. It is the $D_0$ and $D_{max}$ dose rate for each 1000 Ci $^{60}$Co sources at 80-cm distance from the source.

Previously, the dose rate at isocenter 66 for 1,000 Ci $^{60}$Co was calculated as 28 cGy/min when the distance from the $^{60}$C0 source is 80 cm. When each of the five parallel simultaneous beams from the five $^{60}$Co sources in one treatment head 381 reaches at the isocenter 66, they cross fire with similar beams from other three treatment heads also arriving simultaneously at the isocenter 66. Because of the cross firing effects of these simultaneous beams at the isocenter, the biological dose rate of these five simultaneous beams from one treatment head at the isocenter is 28×5, that is 140 cGy/min. There are four treatment heads arranged in a circle at 90° angle distance from each other namely at 0, 90, 180 and 270 degrees apart. There are twenty 1,000 Ci $^{60}$Co beams cross firing at the isocenter 66. As shown before, each of the 1,000 Ci $^{60}$Co beam's isocentric dose rate is 28 cGy/min. Hence the combined biological dose rate of all the 20 simultaneous 1,000 Ci $^{60}$Co beams is 28×20 which is 560 cGy/min.

The $D_0$ dose rate for the Linac is set as 500 cGy/min. Based upon the energy of the Linac x-ray beam, its depth dose at the isocenter will vary. For a simple calculation aimed to show the advantages of these four simultaneous Linac x-ray beams combined with $^{60}$Co beam, the parameters for the dose rate at the isocenter, $D_{iso}$ is kept as the same for 4 MV beam but that was also used to calculate for the $^{60}$Co beam. With the following treatment parameters, average tissue maximum ratio (TMR) 0.746, collimator scatter factor ($S_c$) 0.98, phantom scatter factor ($S_p$) 0.99, has the $D_{iso}$ dose rate of 500×0.98×0.99×0.746 cGy that is 361.88 or 362 cGy/min. Four such beam's additive biological dose rate at the isocenter is 362×4 is 1,448 cGy.

This machine configuration with four treatments heads each with five 1,000 Ci $^{60}$Co sources and there four 20 $^{60}$Co sources and 20 simultaneous beams delivers 560 cGy at isocenter. It's four Linac x-ray simultaneous beams delivers 1,448 cGy at the isocenter. Hence the combined $^{60}$Co and Linear x-ray beam's dose rate at isocenter is 560 plus 1,448 which is 2008 cGy/min. If the single session treatment dose were 800 cGy, and the $^{60}$Co beam delivers 200 cGy and the Linac x-ray beam delivers 600 cGy at the isocenter 66, then their treatment time and monitor unit setup is calculated as the following. Since the combined dose at the isocenter 66 from 20 $^{60}$Co beams from four treatment head is 200 cGy, each of the $^{60}$Co beams delivers 10 cGy at the isocenter. Its dose rate at isocenter is 28 cGy/min. hence its treatment time is $^{10}/_{28}$ that is 0.3571 min or 21.43 seconds. Since its $D_0$ dose is 39 cGy/min, the monitor unit set up is 39×0.3571 which is 13.93 or 14. Since the combined dose at the isocenter 66 from four Linac x-ray treatment head is 600 cGy, each of the Linac-ray beams delivers 150 cGy at the isocenter. Its dose rate at isocenter is 362 cGy/min. Hence its treatment time is $^{150}/_{362}$ that is 0.4144 min or 24.86 or 25 seconds. A patient with no acute respiratory symptoms can hold breathing for this 21 to 25 seconds beam on time. In addition to such short duration single session simultaneous beam treatment associated radiobiological advantages, this short duration beam on time enables breathing synchronized precision radiation therapy much easier.

Figure 4:
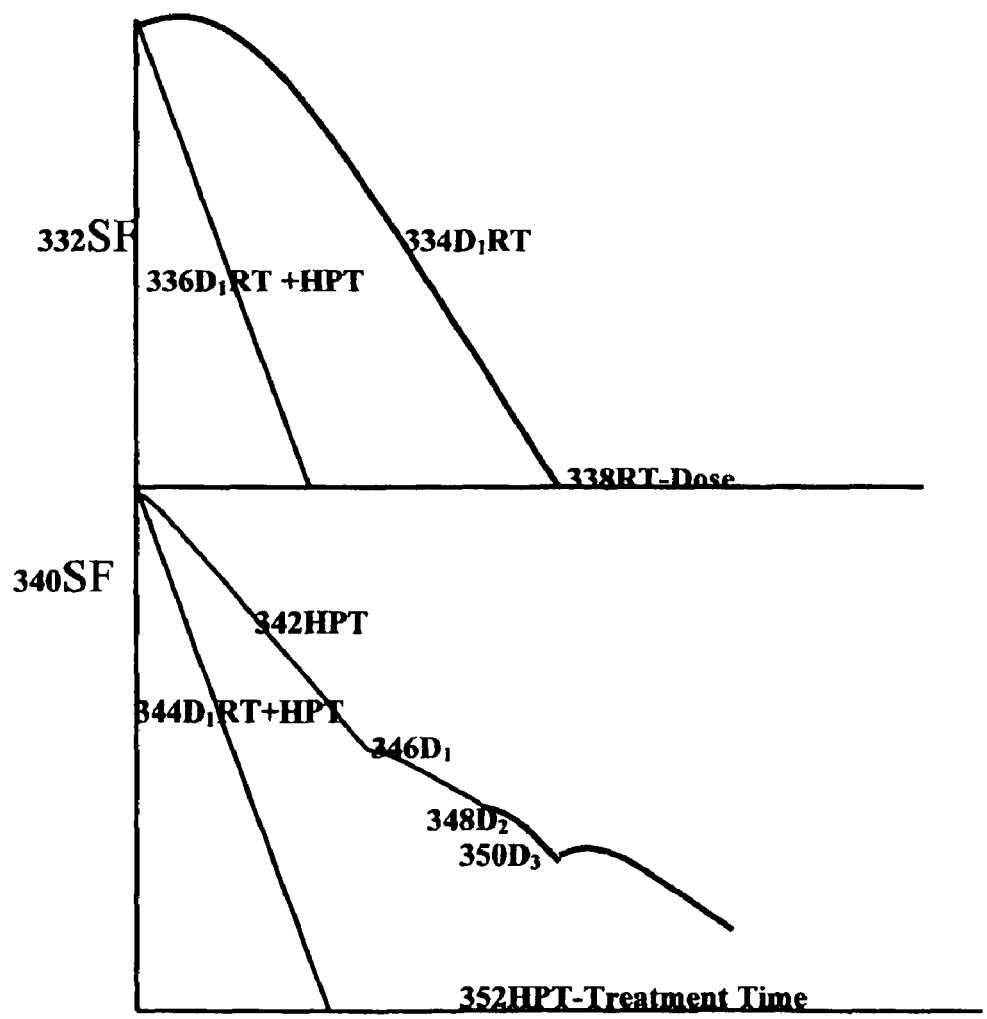
FIG. 4 illustrates a theoretical comparative cell survival curves for single session high dose and high dose rate radiation and multiple dose hyperthermia alone or single session hyperthermia combined with single session high dose and high dose rate radiation.

FIG. 4 illustrates a theoretical comparative cell survival curves for single session high dose and high dose rate radiation and multiple dose hyperthermia alone or single session hyperthermia combined with single session high dose and high dose rate and LET radiation. The survival fraction 332SF is plotted against single session doses 338 RT. The surviving fraction for radiation therapy alone 334$D_1$ RT has a broader shoulder. When the single session high dose and high dose rate radiation is combined with single session hyperthermia, the cell survival curve 336$D_1$ RT+HPT, has a steeper straight-line slope without a shoulder. It is similar to the survival curves for high LET radiation like with neutron.

In lower section of FIG. 4, the surviving fraction for single session hyperthermia plus radiation 340SF is shown. The surviving fraction for first session hyperthermia 342HPT has an initial steeper slope. The survival curve for second session hyperthermia 346$D_1$ has lesser steeper slope. The survival curve for the third session hyperthermia 348$D_2$ has even lesser steeper slope. The survival curve for the fourth session hyperthermia 350$D_3$, has much lesser steeper slope. It is due to development of thermotolerance after the first dose of hyperthermia. The surviving fraction for single session combined high dose, high dose rate and LET radiation and single session hyperthermia 344$D_1$ RT+HPT has a steeper curve like those for high LET radiation Methods of Operation Hyperthermia is administered for 40-60 min with readily available commercial hyperthermia machines like those employing electromagnetic and ultrasound techniques for superficial heating, with interstitial local heating, with interstitial microwave antennas, radiofrequency electrode system, with interstitial ultrasound applicators, intracavitary local heating or with regional and whole body heating machines.

The 40 to 60 min duration hyperthermia is administered during simulation, conformal block making, and treatment planning. If it is combined with image guided surgery and if it will not interfere with surgery, hyperthermia is also administered during the surgical preparation of the patient. If the patient is not under anesthesia, patient is instructed to hold breathing when ready to acquire live CT and MRI images and video of the treatment region. It is most often a single session radiation therapy. Hence most often it is also a single session hyperthermia. The single session hyperthermia overcomes the thermotolerance as when hyperthermia is repeated as in conventional fractionated hyperthermia.

Patient is placed on to the treatment table 174, which is also used as the imaging and treatment table. After adjusting the patient's 172 positioning as in treatment position on the treatment table 174, MV-CT or MRI imaging is done. With the aide of these images, the precise location of the tumor and the region to which radiation is to be delivered is determined. These images are entered into the treatment-planning computer for an onsite treatment planning. The beam on time to radiate a tumor lasts only a few seconds. If the patient is under anesthesia, breathing is controlled while radiation is delivered. If the patient is not under anesthesia and has no respiratory discomfort, then the radiation is delivered while the patient holds the breathing.

The methods of MV-CT and MRI image acquisition are known. Higher quality MV-CT is acquired with multiple simultaneous beams with multiple simultaneous beams from multiple treatment heads. These images are reconstructed by the image-processing computer and projected onto a 3-D stereoscopic LCD monitor as 3-D VR CT or MRI images and onto a 2-D monitor as 2-D CT or MRI images. CT and MRI and PET images if available are fused together. It also includes the scout views of the patient's treatment area. Simultaneous multiple beams are used to radiate multiple treatment fields simultaneously. Their field sizes, dose, beam intensity may vary. Each beam is collimated with primary and secondary collimators. Multiple smaller fields within a smaller field are treated like the "step and shoot" method of treatment with MLC. Individual treatment field is shaped with the field shaping tungsten powder mixture paste.

Each of the treatment head's accessory holders 4 is equipped with the block-forming tray. The beam blocking tungsten powder mixture is made into a thick paste by mixing it with resin that acts like a binder. Methods of such tungsten powder block making are described in previous U.S. patent application Ser. No. 11/974,876 filed on Oct. 15, 2007 (7). Tungsten is non-magnetic and hence it does not interfere with magnetic field environment in which such blocks are made. The height of the blocking material is calculated as in usual field shaping blocks. It blocks over 98 percent of the entering high energy-radiating beam. The beam blocking trays holds the beam blocks. By pushing the paste like blocking material towards the center or away from the center and sculpturing the blocks with the aid of the light fields, the beam blocks are shaped in conformity with the treatment fields. The light field from the treatment head passes through the block on the accessory holder. The treatment heads 2, the accessory holders 4, the block forming trays are all placed away from the patient to minimize and to eliminate the scatter radiation from them reaching the patient on the treatment table 174.

To make the field shaping blocks, the CT or the MRI scout image is projected as 3-D VR image onto stereoscopic and 2-D monitors. If the system has only CT imaging capability, the CT scout image is used in the block making process. If the system has both CT and MRI imaging capability, both are used in the block making process. The light from the treatment head passing through the block on the block-forming tray simulates the beam eye view of the radiating beam. It is projected as the beam passing through the treatment field and falling on to the 3-D VR CT or the MRI image on the stereoscopic screen. It is also projected onto the 2-D monitor.

Pliable block making tungsten powder mixture is inserted into a block-making container and this container is placed on to the accessory holder. It is aligned with the light field like the placement of a field-shaping block on to the accessory holder. The 3-D VR image of the patient's scout view with the tumor is projected on the stereotactic monitor and 2-D view monitor. The beam shaping block's opening is shaped in conformity with each treatment fields. Working with the paste like adjustable block forming material on the block-forming tray, the opening of the block is shaped and adjusted to encompass radiating area with one-cm or fewer margins.

The tungsten powder mixture is pushed forward or backward to increase or decrease the size of the block's opening. For the final adjustment, half a cm per half a cm blocking material is pasted or removed with a long half a-cm width sized spatula. If the field opening is to be decreased, additional blocking material is added at the desired regions within the open area of the beam block. In this case, each 0.3 to 1-cm width blocking material is added with the aid of a blocking material injector. This injector is made to extrude selectable volume of the blocking material ranging from 3 mm to a cm width at a time. Based upon the energy selected, the thickness along the primary beam direction is adjusted to allow only less than 2 percent of the primary beam transmission. Shielding the areas that is outside of the block opening with the jaws further reduces the primary beam transmission through this block. Since this block is made as in continuity without any interruptions in between the paste like blocking material, there is no interleaf transmission of the primary beam as it is with MLC. Conformal field is adjusted by increasing or decreasing the block opening and shaping of the field with the paste like blocking material.

The interleaf transmission of the primary beam by MLC is about 3 percent of the primary beam. The Cerrobend block transmits about 3.5 percent of the primary beam. Computer aided, online treatment planning and dose calculation is made during the treatment process. Multiple beams from varying angles are used for simultaneous treatment of all the treatment fields. Each of the treatment fields is simulated and its shaped field block is made. At the end of all fields shaping, the light fields from all the shaped fields are projected together onto the 3-D and or 4-D VR MR-image on the stereoscopic monitor and to the 2-D monitor to check the combined treatment beam's conformity with the 3-D and or 4-D tumor volume.

At the end of all fields shaping, the light fields from all the shaped fields are projected together onto the 3-D and or 4-D VR MR-image on the stereoscopic monitor and to the 2-D monitor to check the combined treatment beam's conformity with the 3-D and or 4-D tumor volume. If any one of the beams coming from the shaped field is not in conformity with the 3-D or 4-D VR tumor volume and its margin, then it is adjusted by increasing or decreasing the block opening as described above.

Thus the radiation oncologist and the radiation physicists and their team works like a surgeon and a sculptor to shape each of the treatment field's blocks that fits with the tumor volume and its margins so that it fits tightly like a tailor-made attire to do the tight fitting radiosurgery. Such tight fitting radiosurgery helps to radiate the tumor volume and its margins like the surgical resection of a tumor. However, by the surgical resection of a tumor, there are no certainty on the microscopic remnants in the tumor bed and its spread towards its margins. Most often, surgery needs to be followed by radiation to treat the residual tumor and its microscopic spreads. Hence the surgical resection followed by radiation is a two step treatment procedure. On the other hand, the radiosurgery is a single step treatment procedure. It also preserves the functional integrity of an organ much better than treating an organ by surgery. The preservation of the functional integrity of the larynx or the tongue by radiation therapy is a classical example for the difference in functional preservation of an organ by radiation therapy and surgery.

After such block making, repeat CT and or MR-images are taken to check the conformal filed setup that encompasses the entire tumor volume with desired margins. Like before, those images are projected on to the stereotactic 3-D monitor and to 2-D monitor to check the field setups and the beams full coverage of the tumor. If it is found to be satisfactory and if it is a Medical Accelerator system with both CT and MRI, then the CT images are fused with the MRI. Such fused CT-MRI images are used for the treatment planning. If further adjustments in block's opening are needed, then the necessary such adjustments are made before proceeding to switch on the radiating beams.

Like in the present image guided radiation therapy, the treatment-planning computer reconstructs the 2-D images to 3-D images and its segmentations for the treatment planning. Its 3-D VR format is used for treatment planning and dose calculations. Live interactive surface and internal anatomy of the treatment site is projected as 3D-VR-image format with superimposed isodose curves onto the stereoscopic monitor and as 3-D beam's eye view onto the 2-D monitor. Live interactive necessary adjustments are made to the beam's energy if Linac x-ray beams are used and dose rate and beam-weights for each field with the patient in treatment position and ready to be treated.

Intensity Modulated Radiation Therapy to the Entire 3-D-4-D Tumor Volume and its Margins The intensity modulation of the beam for IMRT is done by selection of pencil or divergent beams or $^{60}$Co beam combined with varying energy Linac x-ray beam as divergent or pencil beam. This Medical Accelerator System is equipped with multiple sources for simultaneous beams either from Linac x-ray treatment heads or $^{60}$Co containing treatment heads. The computer generated treatment plan based on the elected energy, pencil or divergent beam, dose rate, field size and the beam weight for each field is used for delivery of few second duration radiation. Additional beam's intensity modulation and beam compensation for missing tissue, inhomogeneity and the curvature of the treatment field on the patient is achieved by simple insertion of minor blocks on the path of the beam. The treatment-planning computer calculates the width and thickness of the blocking material. They provide better intensity-modulated radiation to the entire 3-D tumor volume and its margins.

It has some similarity with multisegmented static field radiation therapy with MLC. However in this instance there are no "step and shoot" delivery methods of radiation though each field's treatment has likeness to the step and shoot method (27). Furthermore, the radiation to the tumor is rendered with much lesser monitor units than when a tumor is treated by the IMRT with MLC. Hence there is much lesser scattered and leakage radiation and thereby much lesser radiation to the normal tissue. It has much more in common with conformal radiation therapy in terms of monitor unit setup, but with much lesser monitor units due to multiple simultaneous beams and their additive biological dose rate and hence much lower scattered and leakage radiation and radiation to the normal tissue.

Delivery of Concomitant Hyperthermia and High Dose and Biological Dose Rate Radiation Therapy and Radiosurgery with the Aid of Interactive Views of Surface and Internal Anatomy by 3-D-MV-CT or MRI Virtual Imaging The method of delivery of hyperthermia is described before. In brief, 40-60 min-individualized hyperthermia is applied with commercially available hyperthermia machines. Hyperthermia is administered during on line simulation, conformal block making, and treatment planning and if it is combined with image guided surgery. As may be needed, patients are anesthetized. Hyperthermia at higher degree is better tolerated under anesthesia. Single session radiotherapy-radiosurgery combined with single session hyperthermia overcomes the hyperthermia's thermotolerance associated lesser effectiveness in tumor cell kill.

The CT or the MRI scout image is projected as 3-D VR image onto stereoscopic and 2-D monitors. The field-light from each source in the treatment head is made in alliance with the block-forming tray. It simulates the beam eye view of the radiating beam. It is projected as the beam passing through the treatment field and falling on to the 3-D VR CT or the MRI image on the stereoscopic screen. It is also projected onto the 2-D monitor. With the aid of these projected beam's eye view light fields, individual blocks for each of the fields are made.

The conformal treatment blocks are constructed with the aid of interactive views of surface and internal anatomy as 3-D-MV-CT or MRI virtual imaging projected on to the stereoscopic screen and onto the 2-D monitor. To make the blocks, the tungsten powder mixture on the tray is pushed forward or backward to increase or decrease the size of the block's opening that is in conformity with the treatment volume per interactive views of surface and internal anatomy projected on to the stereoscopic screen and onto the 2-D monitor. At the end of all field shaping blocks are constructed, the fields-lights are projected on to the field shaping blocks to check the combined treatment beam's conformity with the 3-D volume of the treatment field. If any one of the beams is not in conformity with the 3-D or 4-D VR treatment volume, then it is adjusted by increasing or decreasing the block opening. The computer generated treatment plan based on the elected energy, pencil or divergent beam, dose rate, field size and the beam weight for each field is used for radiating each fields that lasts only a few seconds.

This method of delivery of radiation to a treatment volume has some similarity with multisegmented static field radiation therapy with MLC. However in this instance there is no "step and shoot" delivery (27). Here, radiation to the tumor is rendered with much lesser monitor units than when a tumor is treated by IMRT with MLC. Furthermore, this method of all filed simultaneous treatment of a tumor at the isocenter using multiple beams reduces the monitor unit setup for each field. Hence there is much less combined radiation to the normal tissue from the primary beam and its scattered and leakage radiation.

The present preferred embodiments of this invention are described here; however other modifications could be made without departing from the scope of this invention. The apparatus, methods, procedures and treatments are exemplary and are not intended as limitations on the scope of the invention. Other variations will appear to those skilled in the art and are contemplated to be within the scope of the appended claims.

What is claimed is:

1. Apparatus for image guided high additive dose rate and additive linear energy transfer conformal radiation therapy consisting of a plurality of parallel micro beam generating treatment heads, each configured to emit a radiation beam that passes through an isocentric tumor in a patient, emitting parallel microbeams from all of the plurality of treatment heads simultaneously where the intensity of each of the radiation beam is modulated, a rotating circular gantry with the plurality of parallel micro beam generating treatment heads encased into a circular shield for combined protection from radiation and magnetic field and a mobile, split magnet magnetic resonance imaging system and a cone-beam X-ray system.

2. Apparatus as in claim 1, for imaging with the mobile, split magnet magnetic resonance imaging system and the cone-beam X-ray imaging system.

3. The apparatus of claim 1, where the plurality of parallel micro beam generating treatment heads are fixed to the rotating circular gantry at different angles along the rotating circular gantry.

4. The apparatus of claim 1, where the plurality of parallel micro-beam generating treatment heads are configured to deliver, in combination, a total prescribed radiation dose to the isocentric tumor in one emission of radiation.

5. Apparatus as in claim 1, further consisting of an enclosed chamber that encloses the patient for performing hyperthermia treatment, where hyperthermia treatment includes delivering a total thermal dose to the patient in a single session of applied heat to the patient while the patient is inside the chamber.

6. The apparatus of claim 5, where the plurality of parallel microbeam generating treatment heads are configured to, in combination, deliver a total prescribed radiation dose to the isocentric tumor in one session of radiation, where the single session of applied heat is performed at the same time as the one emission of radiation.

7. The apparatus of claim 5, where the hyperthermia treatment is performed in a single session at the same time as the one emission of radiation in a manner sufficient to inhibit the formation of heat shock protein.

8. The apparatus of claim 5, where the single hyperthermia treatment is performed in a single session at the same time as the one emission of radiation in a manner sufficient to inhibit lethal, and sublethal tissue damage repair, and to inhibit the radiation resistant process of $G_1$ and S-phase DNA synthesis.

9. A method of image guided high additive dose rate conformal radiation therapy combined with hyperthermia consisting of:

a. Providing a plurality of treatment heads, each configured to emit a radiation beam that passes through an isocentric tumor in a patient;
b. positioning a treatment volume in a patient at the isocenter by imaging the treatment region with a mobile, split-magnet magnetic resonance imaging system and a cone-beam X-ray system;
c. emitting radiating beams from the plurality of treatment heads simultaneously, where the intensity of each of the radiation beam is modulated;
d. emitting parallel microbeams from the plurality of treatment heads simultaneously, where the intensity of each of the radiation beam is modulated;
e. applying a single thermal dose of hyperthermia to the target volume simultaneously with step (c);
f. performing functional magnetic resonance spectroscopy with mobile, split-magnet magnetic resonance imaging system;
g. synchronizing step (c) with breath holding of a single respiratory cycle of the patient.

10. A method as in claim 9, where each of the plurality of the treatment heads is LINAC X-ray generators.

11. A method as in claim 9, where each of the plurality of treatment heads is cobalt-60 gamma ray radiation sources.

12. A method as in claim 9, wherein the plurality of the treatment heads are fixed on to a rotating circular gantry at different angles along the rotating circular gantry, and wherein the plurality of the treatment heads are LINAC X-ray generators and cobalt-60 gamma-ray radiation sources.

13. A method as in claim 9, further consisting of forming the parallel microbeams of step (d) by inserting a collimator into the path of the radiation beam of each treatment head.

14. A method of claim 9, further consisting of administering the total dose of radiation to the treatment volume during the breath hold of one respiratory cycle of the patient.

15. The method of claim 9, further consisting of administering step (d) for minimizing damage to normal tissue of the patient.

16. The method claim 9, further consisting of administering step (e) for inhibiting lethal and sublethal damage repair, and $G_1$ and S-phase DNA synthesis.

17. The method of claim 9, further consisting administering step (e) for inhibiting the formation of heat shock proteins.

18. The method of claim 9, further consisting of performing functional magnetic resonance spectroscopy with the mobile, slit-magnetic resonance imaging system in order to acquire dynamic images of cellular interactions during steps (c) or (d).

* * * * *